United States Patent [19]
Sapolsky et al.

[11] Patent Number: 6,027,894
[45] Date of Patent: Feb. 22, 2000

[54] NUCLEIC ACID ADAPTERS CONTAINING A TYPE IIS RESTRICTION SITE AND METHODS OF USING THE SAME

[75] Inventors: Ronald J. Sapolsky; Robert J. Lipshutz, both of Palo Alto; Thomas R. Gingeras, Santa Clara, all of Calif.

[73] Assignee: Affymetrix, Inc., Santa Clara, Calif.

[21] Appl. No.: 09/008,094

[22] Filed: Jan. 16, 1998

Related U.S. Application Data

[63] Continuation of application No. 08/485,606, Jun. 7, 1995, Pat. No. 5,710,000, which is a continuation-in-part of application No. 08/307,881, Sep. 16, 1994, abandoned.

[51] Int. Cl.$^7$ .................................................... C12Q 1/68
[52] U.S. Cl. .......................... 435/6; 435/91.41; 536/24.1; 536/24.2; 536/24.33
[58] Field of Search .................................. 536/24.1, 24.2, 536/24.33; 435/91.41, 6

[56] References Cited

U.S. PATENT DOCUMENTS

| | | |
|---|---|---|
| 5,002,867 | 3/1991 | Macevicz . |
| 5,143,854 | 9/1992 | Pirrung . |
| 5,202,231 | 4/1993 | Dramanc . |
| 5,492,806 | 2/1996 | Drmanac ..................................... 435/5 |
| 5,508,169 | 4/1996 | Deugau . |
| 5,525,464 | 6/1996 | Drmanac ..................................... 435/6 |
| 5,667,972 | 9/1997 | Drmanac ..................................... 435/6 |
| 5,695,940 | 12/1997 | Drmanac ..................................... 435/6 |
| 5,700,637 | 12/1997 | Southern ..................................... 435/6 |
| 5,710,000 | 1/1998 | Saplosky . |

FOREIGN PATENT DOCUMENTS

| | | | |
|---|---|---|---|
| 2036946 | 10/1991 | Canada | .......................... C07H 21/00 |
| WO 90/15070 | 12/1990 | WIPO | .............................. C07K 1/04 |
| WO92/10092 | 6/1992 | WIPO | .............................. A01N 1/02 |

OTHER PUBLICATIONS

Cease et al., *BioTechniques*, vol. 14, Feb. 1993, pp. 250–252, 254 and 255.

U.S. application No. 08/082,937, filed Jun. 25, 1993.

U.S. application No. 08/143,312, filed Oct. 26, 1993.

U.S. application No. 08/284,064, filed Aug. 12, 1994.

Brenner et al., "DNA Fingerprinting by Sampled Sequencing" Proc. Natl. Acad. Sci. USA 86:8902–8906 (1989).

Drmanac, "Genome Sequencing Machine" p. 60 (publication journal and date unknown).

Hoheisel, "Application of Hybridization Techniques to Genome Mapping and Sequencing" Trends in Genetics 10(3):79–83 (1994).

Sapolsky et al., "Mapping Genomic Library Clones using Oligonucleotide Arrays" Hilton Head Conf., SC, Sep. 17–21, 1994.

Smith, "Ligation–Mediated PCR of Restriction Fragments from Large DNA Molecules" PCR Methods and Applications 2:21–27 (Cold Spring Harbor Laboratory Press, 1992).

Szybalski, "Universal Restriction Endonucleases: Designing Novel Cleavage Specificities by Combining Adapter Oligodeoxynucleotide and Enzyme Moieties" Gene 40:169–173 (1985).

Szybalski et al., "Class–IIs Restriction Enzymes: A Review" Gene 100:13–26 (1991).

Unrau et al., "Non–Cloning Amplification of Specific DNA from Whole Genomic DNA Digests using DNA Indexers" Gene 145:163–169 (1994).

*Primary Examiner*—James Ketter
*Attorney, Agent, or Firm*—Townsend and Townsend & Crew

[57] ABSTRACT

The present invention relates to novel methods for sequencing and mapping genetic markers in polynucleotide sequences using Type-IIs restriction endonucleases. The methods herein described result in the "capturing" and determination of specific oligonucleotide sequences located adjacent to Type-IIs restriction sites. The resulting sequences are useful as effective markers for use in genetic mapping, screening and manipulation.

10 Claims, 13 Drawing Sheets

| | cleavage Frequency of first enzyme | sites in λ | size of captured sequence (bp) |
|---|---|---|---|
| AlwI — HgaI | 1/512 | 58 | 5 |
| BbsI — BbvI | 1/2048 | 24 | 6 |
| BsaI — HgaI | 1/2048 | 2 | 5 |
| BseRI — BbvI | 1/2048 | 19 | 8 |
| BsmAI — HgaI | 1/512 | 37 | 5 |
| BspMI — BbvI | 1/2048 | 41 | 8 |
| Esp3I — HgaI | 1/2048 | 14 | 5 |
| EarI — HgaI | 1/2048 | 34 | 4 |
| HgaI — BsmFI | 1/512 | 102 | 10 |
| HphI — BbvI | 1/512 | 168 | 7 |
| MboII — BbvI | 1/512 | 130 | 7 |
| MnlI — HgaI | 1/128 | 262 | 6 |
| PleI — HgaI | 1/512 | 61 | 5 |
| SapI — HgaI | 1/8192 | 10 | 4 |
| SfaNI — FokI | 1/512 | 169 | 9 |

```
                          SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO:1:

CTCTTCTTAA GCGTC                                                    15

(2) INFORMATION FOR SEQ ID NO:2:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (ii) MOLECULE TYPE: DNA (oligonuceotide)

(xi) SEQUENCE DESCRIPTION: SEQ ID NO:2:

CTCTTCNNNN N                                                        11

(2) INFORMATION FOR SEQ ID NO:3:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO:3:

NNNNNGAAGA G                                                        11

(2) INFORMATION FOR SEQ ID NO:4:
```

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:4:

CTGCGNNNNC TTCTC                                               15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (oligonuceotide)

(xi) SEQUENCE DESCRIPTION: SEQ ID NO:5:

CTCTTCNNNN GCGTC                                               15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:6:

GACGCNNNNG AAGAG                                               15

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:7:

GACGCNNNNG                                                     10

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:8:

GACGCNNNNG AAGAG                                               15

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single (D) TOPOLOGY: linear (ii) MOLECULE TYPE: DNA (probe)

(xi) SEQUENCE DESCRIPTION: SEQ ID NO:9:

CTCTTCNNNN                                                                10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:10:

NNNNGAAGAG                                                                10

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:11:

GAGGAGNNNN NNNN                                                           14

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:12:

NNNNNNNNNC TCCTC                                                          14

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:13:

GGATGNNNNN NNNCTCCTC                                                      19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (probe)

```
        (xi) SEQUENCE DESCRIPTION: SEQ ID NO:14:

GAGGAGNNNN NNNNCATCC                                                  19

(2) INFORMATION FOR SEQ ID NO:15:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (probe)

(xi) SEQUENCE DESCRIPTION: SEQ ID NO:15:

AGGAGNNNNN NNNCATCC                                                   18

(2) INFORMATION FOR SEQ ID NO:16:

(i) SEQUENCE CHARACTERISTICS:
             (A) LENGTH: 14 base pairs
             (B) TYPE: nucleic acid
             (C) STRANDEDNESS: single
             (D) TOPOLOGY: linear (ii) MOLECULE TYPE: DNA (probe)

(xi) SEQUENCE DESCRIPTION: SEQ ID NO:16:

GGATGNNNNN NNNC                                                       14

(2) INFORMATION FOR SEQ ID NO:17:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (probe)

(xi) SEQUENCE DESCRIPTION: SEQ ID NO:17:

GGATGNNNNN NNNCTCCT                                                   18
```

NUCLEIC ACID ADAPTERS CONTAINING A TYPE IIS RESTRICTION SITE AND METHODS OF USING THE SAME

This application is a continuation of and claims the benefit of U.S. application Ser. No. 08/485,606 filed Jun. 6, 1995, now U.S. Pat. No. 5,710,000, which is a continuation-in-part of U.S. application Ser. No. 08/307,881, filed Sep. 16, 1994, now abandoned which is hereby incorporated by reference in its entirety for all purposes.

Research leading to the present invention was funded in part by NIH grant Nos. 5-F32-HG00105 and RO1 HG00813-02, and the government may have certain rights to the invention.

The present invention generally relates to novel methods for isolating, characterizing and mapping genetic markers in polynucleotide sequences. More particularly, the present invention provides methods for mapping genetic material using Type-IIs restriction endonucleases. The methods herein described result in the "capturing" and determination of specific oligonucleotide sequences located adjacent to Type-IIs restriction sites. The resulting sequences are useful as effective markers for use in genetic mapping, screening and manipulation.

BACKGROUND OF THE INVENTION

The relationship between structure and function of macromolecules is of fundamental importance in the understanding of biological systems. These relationships are important to understanding, for example, the functions of enzymes, structural proteins and signaling proteins, ways in which cells communicate with each other, as well as mechanisms of cellular control and metabolic feedback.

Genetic information is critical in continuation of life processes. Life is substantially informationally based and its genetic content controls the growth and reproduction of the organism and its complements. The amino acid sequences of polypeptides, which are critical features of all living systems, are encoded by the genetic material of the cell. Further, the properties of these polypeptides, e.g., as enzymes, functional proteins, and structural proteins, are determined by the sequence of amino acids which make them up. As structure and function are integrally related, many biological functions may be explained by elucidating the underlying structural features which provide those functions, and these structures are determined by the underlying genetic information in the form of polynucleotide sequences. Further, in addition to encoding polypeptides, polynucleotide sequences also can be involved in control and regulation of gene expression. It therefore follows that the determination of the make-up of this genetic information has achieved significant scientific importance.

Physical maps of genomic DNA assist in establishing the relationship between genetic loci and the DNA fragments which carry these loci in a clone library. Physical maps include "hard" maps which are overlapping cloned DNA fragments ("contigs") ordered as they are found in the genome of origin, and "soft" maps which consist of long range restriction enzyme and cytogenetic maps (Stefton and Goodfellow, 1992). In the latter case, the combination of rare cutting restriction endonucleases (e.g., NotI) and pulse gel electrophoresis allows for the large scale mapping of genomic DNAs. These methods provide a low resolution or top down approach to genomic mapping.

A bottom up approach is exemplified by construction of contiguous or "contig" maps. Initial attempts to construct contig maps for the human genome have been based upon ordering inserts cloned into cosmids. More recent studies have utilized yeast artificial chromosomes (YACs) which allow for cloning larger inserts. The construction of contig maps require that many clones be examined (4–5 genome equivalents) in order to assure that sufficient overlap between clones is achieved. Currently, four approaches are used to identify overlapping sequences.

The first method is restriction enzyme fingerprinting. This method involves the electrophoretic sizing of restriction enzyme generated DNA fragments for each clone and establishing a criterion for clone overlap based on the similarity of fragment sets produced for each clone. The sensitivity and specificity of this approach has been improved by labelling of fragments using ligation, and end-filling techniques. The detection of repetitive sequence elements (e.g., $[GT]_n$) has also been employed to provide characteristic markers.

The second method generally employed in mapping applications is the binary scoring method. This method involves the immobilization of members of a clone library to filters and hybridization with sets of oligonucleotide probes. Several mathematical models have been developed to avoid the need for large numbers of the probe sets which are designed to detect the overlap regions.

A third method is the Sequence Tagged Site ("STS") method. This method employs PCR techniques and gel analysis to generate DNA products whose lengths characterize them as being related to common regions of sequence that are present in overlapping clones. The sequence of the primary pairs and the characteristic distance between them provides sufficient information to establish a single copy landmark (SCL) which is analogous to single copy probes that are unique in the entire genome.

A fourth method uses cross-hybridizing libraries. This method involves the immobilization of two or more pools of cosmid libraries followed by cross-hybridization experiments between pairs of the libraries. This cross-hybridization demonstrates shared cloned sequences between the library pairs. See, e.g., Kupfer, et al., (1995) Genomics 27:90–100.

Although each of these methods is capable of generating useful physical maps of genomic DNA, they each involve complex series of reaction steps including multiple independent synthesis, labelling and detection procedures.

Traditional restriction endonuclease mapping techniques, i.e., as described above, typically utilize restriction enzyme recognition/cleavage sites as genetic markers. These methods generally employ Type-II restriction endonucleases, e.g., EcoRI, HindIII and BamHI, which will typically recognize specific palindromic nucleotide sequences, or restriction sites, within the polynucleotide sequence to be mapped, and cleave the sequence at that site. The restriction fragments which result from the cleavage of separate fragments of the polynucleotide (i.e., from a prior digestion) are then separated by size. overlap is shown where restriction fragments of the same size appear from Type-II endonuclease digestion of separate polynucleotide fragments.

Type-IIs endonucleases, on the other hand, generally recognize non-palindromic sequences. Further, these endonucleases generally cleave outside of their recognition site, thus producing overhangs of ambiguous base pairs. Szybalski, 1985, Gene 40:169–173. Additionally, as a result of their non-palindromic recognition sequences, the use of Type-IIs endonucleases will generate more markers per Kb than a similar Type-II endonuclease, e.g., approximately twice as often.

The use of Type-IIs endonucleases in mapping genomic markers has been described in, e.g., Brenner, et al., P.N.A.S. 86:8902–8906 (1989). The methods described involved cleavage of genomic DNA with a Type-IIs endonuclease, followed by polymerization with a mixture of the four deoxynucleotides as well as one of the four specific fluorescently labelled dideoxynucleotides (ddA, ddT, ddG or ddC). Each successive unpaired nucleotide within the overhang of the Type-IIs cleavage site would be filled by either a normal nucleotide or the labelled dideoxynucleotide. Where the latter occurred, polymerization stopped. Thus, the polymerization reaction yields an array of double stranded fluorescent DNA fragments of slightly different sizes. By reading the size from smallest size to largest, in each of the nucleotide groups, one can determine the specific sequence of the overhang. However, this method can be time consuming and yields only the sequence of the overhang region.

Oligonucleotide probes have long been used to detect complementary nucleic acid sequences in a nucleic acid of interest (the "target" nucleic acid). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid. See, e.g., U.S. patent application Ser. No. 08/082,937, filed Jun. 25, 1993, which is incorporated herein by reference. Others have proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231 and 5,002,867.

The development of VLSIPS™ (Very Large Substrate Immobilized Polymer Synthesis) technology has provided methods for making very large combinations of oligonucleotide probes in very small arrays. See U.S. Pat. No. 5,143,854 and PCT patent publication Nos. WO 90/15070 and 92/10092, each of which is incorporated herein by reference in its entirety for all purposes. U.S. patent application Ser. No. 08/082,937, incorporated above, also describes methods for making arrays of oligonucleotide probes that can be used to provide the complete sequence of a target nucleic acid and to detect the presence of a nucleic acid containing a specific nucleotide sequence.

The construction of genetic linkage maps and the development of physical maps are essential steps on the pathway to determining the complete nucleotide sequence of the human or other genomes. Present methods used to construct these maps rely upon information obtained from a range of technologies including gel-based electrophoresis, hybridization, polymerase chain reaction (PCR) and chromosome banding. These methods, while providing useful mapping information, are very time consuming when applied to very large genome fragments or other nucleic acids. There is therefore a need to provide improved methods for the identification and correlation of genetic markers on a nucleic acid which can be used to rapidly generate genomic maps. The present invention meets these and other needs.

SUMMARY OF THE INVENTION

The present invention provides methods for identifying specific oligonucleotide sequences using Type-IIs endonucleases in sequential order to capture the ambiguous sequences adjacent to the Type-IIs recognition sites. These ambiguous sequences can then be probed sequentially with probes specific for the various combinations of possible ambiguous base pair sequences. By determining which probe hybridizes with an ambiguous sequence, that sequence is thus determined. Further, because that sequence is adjacent to a specific Type-IIs cleavage site that portion of the sequence is also known. This contiguous sequence is useful as a marker sequence in mapping genomic libraries.

In one embodiment, the present invention provides a method of identifying sequences in a polynucleotide sequence. The method comprises cleaving the polynucleotide sequence with a first type-IIs endonuclease. A first adapter sequence, having a recognition site for a second type-IIs endonuclease, is ligated to the polynucleotide sequence cleaved in the first cleaving step. The polynucleotide sequence resulting from the first ligating step, is cleaved with the second type-IIs endonuclease, and a second adapter sequence is ligated to the polynucleotide sequence cleaved in the second cleaving step. The sequence of nucleotides of the polynucleotide sequence between the first and second adapter sequences is then determined.

In another embodiment, the present invention provides a method of generating an ordered map of a library of genomic fragments. The method comprises identifying sequences in each of the genomic fragments in the library, as described above. The identified sequences in each fragment are compared with the sequences identified in each other fragment to obtain a level of correlation between each fragment and each other fragment. The fragments are then ordered according to their level of correlation.

In a further embodiment, the present invention provides a method of identifying polymorphisms in a target polynucleotide sequence. The method comprises identifying sequences in a wild-type polynucleotide sequence, according to the methods described above. The identifying step is repeated on the target polynucleotide sequence. The differences in the sequences identified in each of the identifying steps are determined, the differences being indicative of a polymorphism.

In still another embodiment, the present invention provides a method of identifying a source of a biological sample. The method comprises identifying a plurality of sequences in a polynucleotide sequence derived from the sample, according to the methods described herein. The plurality of sequences identified in the identifying step are compared with a plurality of sequences identically identified from a polynucleotide derived from a known source. The identity of the plurality of sequences identified from the sample with the plurality of sequences identified from the known source is indicative that the sample was derived from the known source.

In an additional embodiment, the present invention provides a method of determining a relative location of a target nucleotide sequence on a polynucleotide. The method comprises generating an ordered map of the polynucleotide according to the methods described herein. The polynucleotide is fragmented. The fragment which includes the target nucleotide sequence is then determined, and a marker on the fragment is correlated with a marker on the ordered map to identify the approximate location of the target nucleotide sequence on the polynucleotide.

BRIEF DESCRIPTION OF THE DRAWINGS

FIG. 1 shows examples of combinations of Type-IIs endonucleases useful in the present invention. Gaps in the sequence illustrate the cleavage pattern of the first Type-IIs, endonuclease, shown to the left, whereas arrows illustrate the cleavage points of the second Type-IIs endonuclease, shown to the right, when the recognition site for that endonuclease is ligated to the first cleaved sequence. FIG. 1 also shows the expected frequency of cleavage of the first Type-IIs endonuclease, the number of recognition sites in λ DNA, and the size of the sandwiched sequence.

DESCRIPTION OF THE PREFERRED EMBODIMENT

Figure 2:
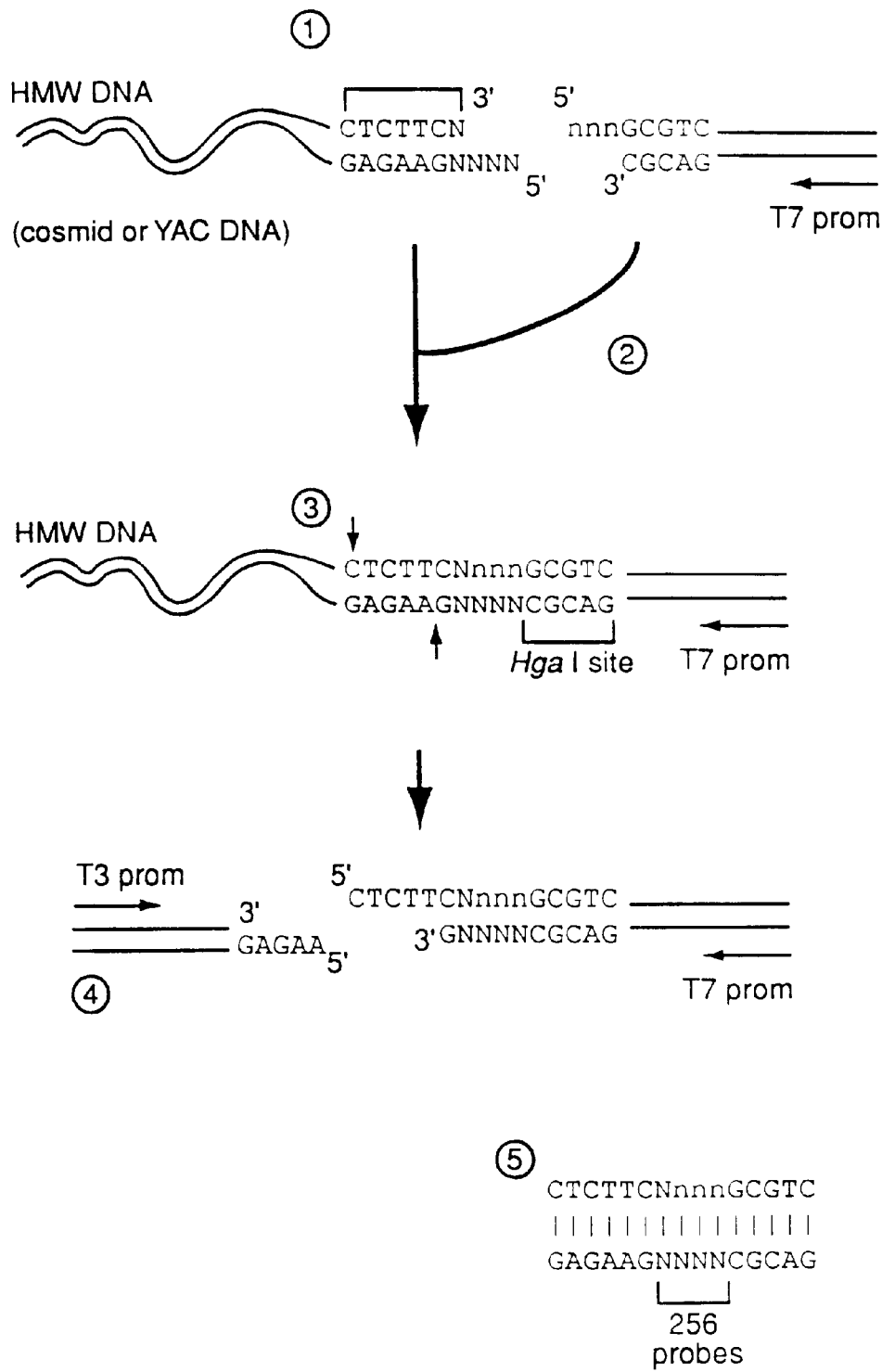
FIG. 2 shows a schematic representation of an embodiment of the present invention for capturing Type-IIs restriction sites showing (1) a first cleavage with EarI, (2) followed by a ligation to the 5' overhang of a first adapter sequence, (3) cleavage with HgaI, (4) ligation to second adapter sequence followed by PCR amplification (5).

In general, the present invention provides novel methods for identifying and characterizing sequence based nucleic acid markers as well as a method for determining their presence. The methods may generally be used for generating maps for large, high molecular weight nucleic acids, i.e., for mapping short clones, cosmids, YACs, as well as in methods for genetic mapping for entire genomes. Generally, the methods of the present invention involve the capturing of ambiguous nucleic acid sequence segments using sequential cleavage with restriction endonucleases. In particular, the methods of the invention include a first cleavage which leaves ambiguous sequences downstream from the recognition site of the cleavage enzyme. A second type-IIs recognition site is ligated to the target sequence, and a second cleavage, recognizing the second site, cleaves upstream from the first cleavage site, within the first recognition site, resulting in short sequences which contain the recognition site and an ambiguous sequence "captured" from the target sequence, between the two cleavage sites. The combination of the recognition site and the captured sequences are particularly useful as genetic markers for genomic mapping applications.

In one embodiment, the methods of the present invention comprise the use of type-IIs endonucleases to capture sequences adjacent to the type-IIs recognition site. These captured sequences then become effective sequence based markers. More particularly, this method comprises first treating the polynucleotide sequence with a first Type-IIs endonuclease having a specific recognition site on the sequence, thereby cleaving the sequence. A first "adapter sequence" which comprises a second Type-IIs endonuclease recognition site is ligated to the cleaved sequence. The resulting heterologous sequence thus has an ambiguous sequence sandwiched between two different Type-IIs endonuclease recognition sites. This resulting sequence is then treated with a second Type-IIs endonuclease specific for the ligated recognition site, thereby cleaving the sequence. A second adapter sequence is then ligated to this cleaved sequence. The sequence resulting from this ligation is then probed to determine the sequence of the sandwiched, or "captured", ambiguous sequence.

I. Type-IIs Endonucleases

Type-IIs endonucleases are generally commercially available and are well known in the art. Like their Type-II counterparts, Type-IIs endonucleases recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end."

Type-II endonucleases, however, generally require that the specific recognition site be palindromic. That is, reading in the 5' to 3' direction, the base pair sequence is the same for both strands of the recognition site. For example, the sequence

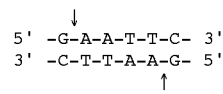

is the recognition site for the Type-II endonuclease EcoRI, where the arrows indicate the cleavage sites in each strand. This sequence is palindromic in that both strands of the sequence, when read in the 5t to 3' direction are the same.

The Type-IIs endonucleases, on the other hand, generally do not require palindromic recognition sequences. Additionally, these Type-IIs endonucleases also generally cleave outside of their recognition sites. For example, the Type-IIs endonuclease EarI recognizes and cleaves in the following manner:

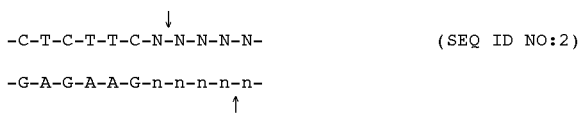

(SEQ ID NO:2)

where the recognition sequence is -C-T-C-T-T-C-, N and n represent complementary, ambiguous base pairs and the arrows indicate the cleavage sites in each strand. As the example illustrates, the recognition sequence is non-palindromic, and the cleavage occurs outside of that recognition site. Because the cleavage occurs within an ambiguous portion of the polynucleotide sequence, it permits the capturing of the ambiguous sequence up to the cleavage site, under the methods of the present invention.

Specific Type-IIs endonucleases which are useful in the present invention include, e.g., EarI, MnlI, PleI, AlwI, BbsI, BsaI, BsmAI, BspMI, Esp3I, HgaI, SapI, SfaNI, BbvI, BsmFI, FokI, BseRI, HphI and MboII. The activity of these Type-IIs endonucleases is illustrated in FIG. 1, which shows the cleavage and recognition patterns of the Type-IIs endonucleases.

II. Capturing Ambiguous Sequences Adjacent to Type-IIs Restriction Sites

Figure 3:
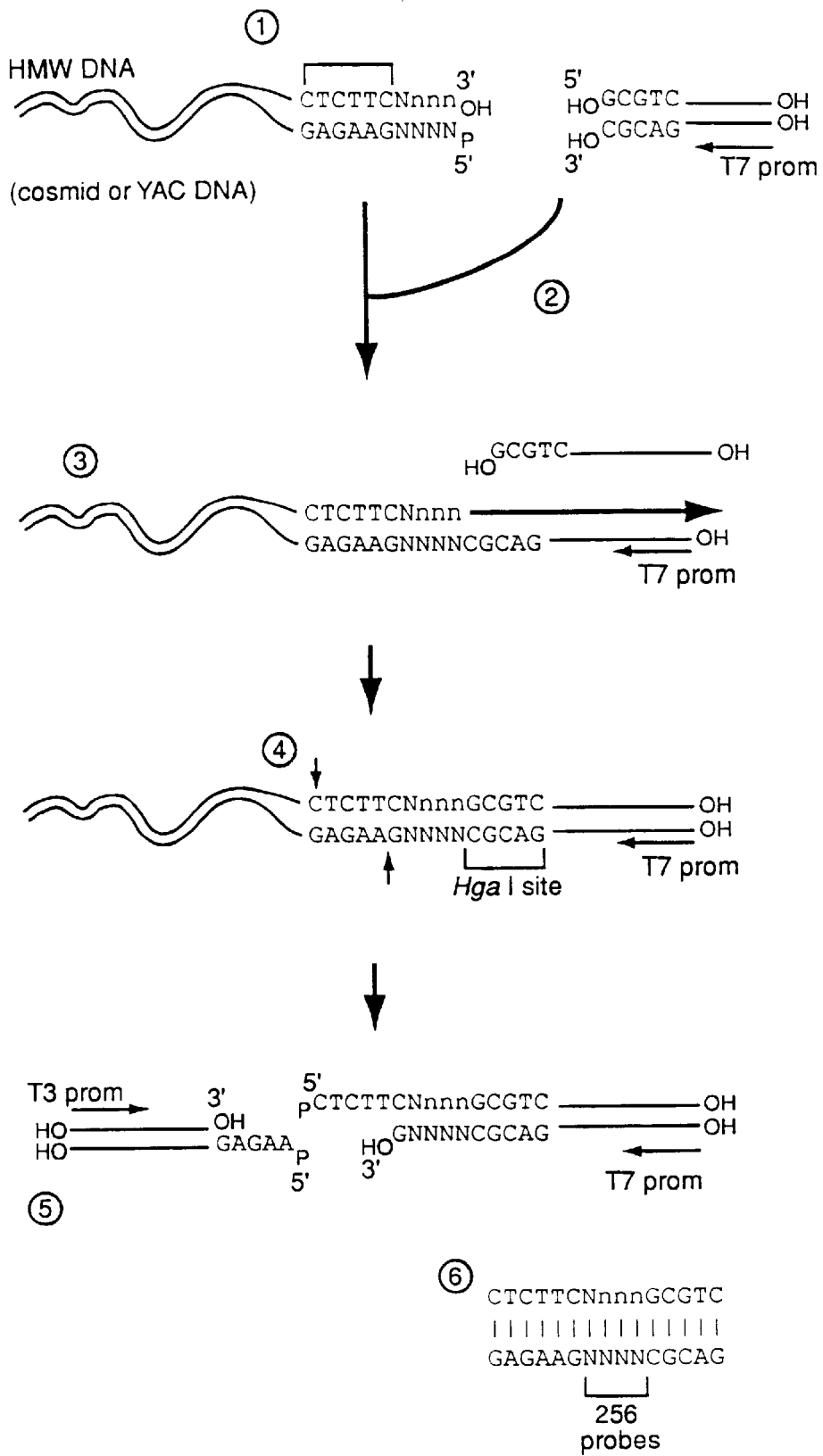
FIG. 3 shows a schematic representation of a preferred embodiment of the present invention using (1) a first cleavage with EarI followed by DNA polymerization of the overhang to yield a blunt end, (2) ligation to blunt end first adapter sequence, (3) melting off the unligated adapter strand followed by DNA polymerization to extend dsDNA across the first adapter strand, (4) cleavage with HgaI at the EarI recognition site, (5) ligation of second adapter sequence to target sequence, and (6) amplification/transcription of the captured target sequence.

A general schematic of the capturing of the ambiguous sequences is shown in FIGS. 2 and 3.

Treatment of the polynucleotide sequence sought to be mapped with a Type-IIs endonuclease, results in a cleaved sequence having a number of ambiguous, or unknown, nucleotides adjacent to a Type-IIs endonuclease recognition site within the target sequence. Additionally, within this ambiguous region, an overhang is created. The recognition site and the ambiguous nucleotides are termed the "target sequence." The overhang may be 2, 3, 4 or 5 or more nucleotides in length while the ambiguous sequence may be from 4 to 9 or more nucleotides in length, both of which will depend upon the Type-IIs endonucleases used. Examples of specific Type-IIs endonucleases for this first cleavage include BsmAI, EarI, MnlI, PleI, AlwI, BbsI, BsaI, BspMI, Esp3I, HgaI, SapI, SfaNI, BseRI, HphI and MboII. Again, these first Type-IIs endonucleases and their cleavage patterns are shown in FIG. 1, where the shaded region to the left illustrates the recognition site of the first Type-IIs endonuclease, and gaps in the sequence illustrate the cleavage pattern of the enzyme. Cleavage of high molecular weight DNA with EarI leaves an overhang of three ambiguous base pairs, as shown in FIGS. 2 and 3, step 1. The recognition site of EarI is indicated by the bar. Thus, EarI cleavage of the target nucleic acid will produce a sequence having the following cleavage end:

(SEQ ID NO:2)

The overhanging bases are then filled in. This is preferably carried out by treatment of the target sequence with a DNA polymerase, such as Klenow fragment or T4 DNA polymerase, resulting in a blunt end sequence as shown in FIG. 3, step 1. Alternatively however, the overhang may be filled by the hybridization of this overhang with an adapter sequence having an overhang complementary to that of the target sequence, as shown in FIG. 2, step 2. A tagging scheme, similar to this latter method has been described. See, D. R. Smith, PCR Meth. and Appl. 2:21–27 (1992).

Following cleavage and fill in of the overhang portion, an adapter sequence is typically ligated to the cleavage end. The adapter sequences described in the present invention generally are specific polynucleotide sequences prepared for ligation to the target sequence. In preferred embodiments, these sequences will incorporate a second type-IIs restriction site. Ligation of an adapter including a HgaI recognition site is shown in FIGS. 2 and 3, step 2. The adapter sequences are generally prepared by oligonucleotide synthesis methods generally well known in the art, such as the phosphoramidite or phosphotriester methods described in, e.g., Gait, Oligonucleotide Synthesis: A Practical Approach, IRL Press (1990).

An adapter sequence prepared to include a second type-IIs recognition site, for example, the HgaI recognition site 3'-C-G-C-A-G-5' would be ligated to the cleaved target sequence to provide a cleavage site on the other end of the ambiguous sequence. For example, ligation of the HgaI adapter to the target sequence would produce the following sequence having the cleavage pattern shown:

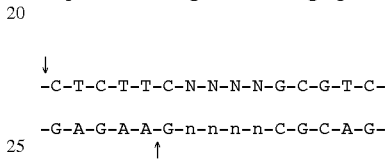

In addition to the Type-IIs recognition sites, preferred adapter sequences will also generally include PCR primers and/or promoter sequences for in vitro transcription, thereby facilitating amplification and labeling of the target sequence.

The method of ligation of the first adapter sequence to the target sequence may be adapted depending upon the particular embodiment practiced. For example, where ligation of the first adapter sequence is to the overhang of the target sequence, as shown in FIG. 2, step 2, the adapter sequence will generally comprise an overhang which is complementary to the overhang of the target sequence. For this embodiment, a mixture of adapter sequences would generally be used wherein all possible permutations of the overhang are present. For example, the number of specific probe sequences will typically be about $4^m$ where m is the number of overhanging nucleotides. For example, where the target sequence after the first cleavage has a 4 base pair overhang of ambiguous nucleotides, the mixture of sequences would typically comprise adapters having upwards of $4^4$, or 256 different overhang sequences. Where the overhang in question includes greater numbers of nucleotides, the adapters would generally be provided in two or more separate mixtures to minimize potential ligation of the adapters within each mixture. For example, one set of adapters may incorporate a pyrimidine nucleotide in a given position of the overhang for all adapters in the mixture whereas the other set will have a purine nucleotide in that position. As a result, ligation of the adapters to adapters in the same mixture will be substantially reduced. For longer overhang sequences, it may often be desirable to provide additional separate mixtures of adapters. Ligation of the adapter sequence to the target sequence is then carried out using a DNA ligase according to methods known in the art.

Where the overhang of the target sequence is filled in by Klenow fragment polymerization, as in FIG. 3, step 1, a blunt end adapter sequence is ligated to the target sequence. See, FIG. 3, step 2. Because a blunt end ligation is used rather than an overhang, a mixture of hybridizable sequences is unnecessary, and a single adapter sequence is used. Further, this method avoids any hybridization between the overhangs in the mixture of adapter sequences.

Using this method, the polymerized target sequence will be phosphorylated on only the 5' strand. Further, as the adapter will have only 3' and 5' hydroxyls for ligation, only the 3' end of the adapter will be ligated to the blunt, phosphorylated 5' end of the target sequence, leaving a gap in the other strand. The unligated strand of the adapter sequence may then be melted off and the remaining polynucleotide again treated with DNA polymerase, e.g., Klenow or *E. coli* DNA polymerase, as shown in FIG. 3, step 3, resulting in a double-stranded, heterologous polynucleotide. This polynucleotide has the ambiguous nucleotide sequence sandwiched between the first Type-IIs endonuclease recognition site ("site A"), and the second, ligated Type-IIs recognition site ("site B"). One skilled in the art will recognize that approximately half of the adapter sequences will ligate to the target sequence in an inverted orientation. However, this does not affect the results of the methods of the present invention due to the inability of the second type-IIs enzyme to cleave the target sequence in those cases where the adapter is inverted. This is discussed in greater detail, below.

The polynucleotide resulting from ligation of this first adapter sequence to the target sequence is then treated with a second Type-II endonuclease specific for the ligated recognition site B. This second endonuclease treatment cleaves the remainder of the original polynucleotide from the target sequence. In preferred aspects, the second type-IIs endonuclease will be selected, or the second recognition site will be positioned within the adapter sequence, whereby the cleavage pattern of the second Type-IIs endonuclease results in the second cleavage substantially or entirely overlapping the first recognition site A, i.e., the cleavage of each strand is within or adjacent to the first recognition site (site A). FIG. 2, step 3, and FIG. 3, step 4 show the cleavage of the polynucleotide using HgaI (the HgaI recognition site is shown by the bar). Where the adapter sequence is ligated in a reverse orientation, as previously noted, no cleavage will occur within the first recognition site, as the recognition site will be at the distal end of the adapter sequence. Further, any primer sequences present within this adapter will be inverted preventing subsequent amplification. By selecting a second Type-IIs endonuclease different from the first, recleavage of the first cleavage site is avoided. Selection of an appropriate type-IIs endonuclease for the second cleavage, and thus, the appropriate recognition site for the first adapter sequence, may often depend upon the first endonuclease used, or as described above, the position of the recognition site within the adapter. In preferred aspects, the first and second type-IIs endonucleases are selected whereby the second endonuclease cleaves entirely within the first endonucleases recognition sequence. Examples of Type-IIs endonucleases for the second cleavage generally include those described above, and are typically selected from HgaI, BbvI, BspMI, BsmFI and FokI. Particularly preferred combinations of Type-IIs endonucleases for the first and second cleavages, as well as their cleavage patterns are shown in FIG. 1. Continuing with the previous example, HgaI cleavage of the sample target sequence would produce the following sequence having the ambiguous base pairs captured by the first adapter sequence:

-C-T-C-T-T-C-N-N-N-G-C-G-T-C-
     -G-n-n-n-n-C-G-C-A-G-

Depending upon the type-IIs endonucleases used in each step, the sequence of the overhang is known. For example, in the above example, the HgaI cleavage site for the second endonuclease is within the first endonuclease's recognition site, e.g., the EarI site. An example of a known overhang sequence is demonstrated in FIGS. 2 and 3, steps 4 and 5, respectively.

As noted, in the preferred aspects the second cleavage site substantially or entirely overlaps the first recognition site A. Accordingly, the number of possible hybridizing sequences for this ligation step is rendered unique. The specific recognition site A of the first Type-IIs endonuclease is known. Thus, where the second cleavage occurs entirely within the first recognition site A, only the unique sequences hybridizing to that sequence would be used. On the other hand, where the second cleavage occurs to some extent outside of the first recognition site A, a mixture of specific adapter sequences hybridizable to all possible permutations of nucleotides outside of site A is used. For example, where cleavage incorporates one nucleotide outside of the first recognition site, the four variations to the known sequence are possible and a mixture of adapter sequences hybridizable to all four is used (See, e.g., MnlI-HgaI enzyme pairing in FIG. 1). The number of bases included in the second cleavage which fall outside the first recognition site is readily determinable from the endonucleases used.

As with the first adapter sequence, the second adapter sequence may comprise a PCR primer sequence and/or a promoter sequence for in vitro transcription.

The resulting target sequence will thus have the target sequence, specifically, an ambiguous sequence attached to a portion or all of the first recognition site, sandwiched or captured between the two adapter sequences. For example, the resulting target sequence will generally have the general sequence:

(Adapter sequence/A)-(Ambiguous sequence)-(B/Adapter sequence)

where A is a portion or all of the recognition site for the first Type-IIs endonuclease, and B is the recognition site for the second Type-IIs endonuclease. Again, applying the previous example, the resulting target sequence would appear as follows:

Adapter 2 -C-T-C-T-T-C-N-N-N-N-G-C-G-T-C- Adapter 1

Adapter 2'-G-A-G-A-A-G-n-n-n-n-C-G-C-A-G- Adapter 1'

The sequence -C-T-C-T-T-C-N-N-N-N- is captured from the original target sequence and sandwiched between the two adapter sequences.

Prior to probing, the target sequence will generally be amplified to increase the detectability of the sequence. Amplification is generally carried out by methods well known in the art. See FIGS. 2 and 3, steps 5 and 6, respectively. For example, amplification may be performed by way of polymerase chain reaction (PCR) using methods generally well known in the art. See, e.g., Recombinant DNA Methodology, Wu, et al., ed., Academic Press (1989), Sambrook, et al., Molecular Cloning: A Laboratory Manual (2nd ed.), vols. 1–3, Cold Spring Harbor Laboratory, (1989), Current Protocols in Molecular Biology, F. Ausubel, et al., ed., Greene Publishing and Wiley Interscience, New York (1987 and periodic updates). As described earlier, this amplification may be facilitated by the incorporation of specific primer sequences or complements within the adapters. Further, such amplification may also incorporate a label into the amplified target sequence. In a preferred embodiment, the target sequence may be amplified using an asymmetric PCR method whereby only the strand comprising the appropriate recognition site A is amplified. Asymmetric amplification is generally carried out by use of primer which will initiate amplification of the appropriate strand of the target sequence, i.e., the target sequence.

The amplified target sequence may then be probed using specific oligonucleotide probes capable of hybridizing to the (A)-(ambiguous sequence)-(B) target sequence. As both the A and B sequences are set by the capturing method and are known, the probes need only differ with respect to the ambiguous portion of the sequence to be probed. For example, using the example sequence provided above, assuming that one is probing with the top strand, e.g., the bottom strand was amplified by appropriate selection of primers, etc., the probes would generally have the sequence C-T-C-T-T-C-n-n-n-n-G-C-G-T-C, where n denotes every possible base at the particular position, e.g., A, T, G, C. The preparation of oligonucleotide probes is performed by methods generally known in the art. See, Gait, Oligonucleotide Synthesis: A Practical Approach, IRL Press (1990). Additionally, these oligonucleotide probes may'be labelled, i.e., fluorescently or radioactively, so that probes which hybridize with target sequences can be detected. In preferred aspects, however, the probes will be immobilized, and it will be the target that is labelled. Labelling of the target sequence may be carried out using known methods. For example, amplification of the target sequence can incorporate a label into the amplified target sequence, e.g., by use of a labelled PCR primer or by incorporating a label during in vitro transcription of either strand.

In the preferred embodiment of the present invention, the target sequence is probed using an oligonucleotide array. Through the use of these oligonucleotide arrays, the specific hybridization of a target sequence can be tested against a large number of individual probes in a single reaction. Such oligonucleotide arrays employ a substrate, comprising positionally distinct sequence specific recognition reagents, such as polynucleotides, localized at high densities. A single array can comprise a large number of individual probe sequences. Further, because the probes are in known positionally distinct orientations on the substrate, one need only examine the hybridization pattern of a target oligonucleotide on the substrate to determine the sequence of the target oligonucleotide. Use and preparation of these arrays for oligonucleotide probing is generally described in PCT patent publication Nos. WO 92/10092, WO 90/15070, U.S patent application Ser. Nos. 08/143,312 and 08/284,064. Each of these references is hereby incorporated by reference in its entirety for all purposes.

As noted, the target sequence will have the general sequence:

(Adapter sequence/A)-($N_k$)-(B/Adapter sequence)

where $N_k$ denotes the ambiguous sequence of nucleotides of length k, and the nucleotide sequence of each adapter sequence is known and the sequence of sites A and B are known. Only the nucleotide sequence of the ambiguous portion of the target sequence, $N_k$ is not known. Thus, the number of probes required on the array substrate is generally related to the number of ambiguous nucleotides in the target sequence. In one embodiment, the number of potential sequences for an ambiguous sequence is $4^k$, where k is the number of ambiguous bases within the sequence. For example, where there are four ambiguous nucleotides within the target sequence, the array would generally include about $4^4$ or 256 or more separate probes, where each probe will include the general sequence:

(A')-($N'_k$)-(B')

where "A'" and "B'" are the complements to site-A and site-B of the target sequence, respectively and are constant throughout the array, and "$N'_k$" generally represents all potential sequences of the length of the ambiguous sequence of the target sequence. Thus, where the ambiguous sequence contains, e.g., $4^4$ nucleotides, "$N'_k$" would typically include, for example, $4^4$ different sequences, at least one of which will hybridize with the target sequence. On an oligonucleotide array, this is accomplished through a simple combinatorial array like that shown in FIG. 4. Typically, as the size of the ambiguous sequence increases, the number of probes on the array will also increase, e.g., where the ambiguous sequence is 8 bases long, their will typically be about $4^8$ or 65,536 probes on the array.

In the case of high molecular weight nucleic acids, the original polynucleotide sequence will generally comprise more than one and even several specific Type-IIs endonuclease recognition/cleavage sites, e.g., EarI sites. As a result, a number of ambiguous sequence segments will be captured for a given polynucleotide. Upon probing with an oligonucleotide array, the sequence will hybridize with a number of probes which are complementary to all of the captured sequences, producing a distinctive hybridization pattern for the given polynucleotide sequence. The specific hybridization pattern of the target sequence upon the array will generally indicate the ambiguous sequences adjacent to all of the cleavage sites as was described above.

III. Mapping Genomic Libraries

A. Physical Maps

A further embodiment of the present invention provides a method for the ordered mapping of genomic libraries. Typically, the term "genomic library" is defined as a set of sequence fragments from a larger polynucleotide fragment. Such larger fragments may be whole chromosomes, subsets thereof, plasmids, or other similar large polynucleotides. Specifically, the methods of the present invention are useful for mapping high molecular weight polynucleotides including chromosomal fragments, cosmids and Yeast Artificial Chromosomes (YACs).

Mapping techniques typically involve the identification of specific genetic markers on individual polynucleotide fragments from a genomic library. Comparison of the presence and relative position of specific markers on fragments generated by different cleavage patterns allows for the assembly of a contiguous genomic map, or "contig".

Figure 6:
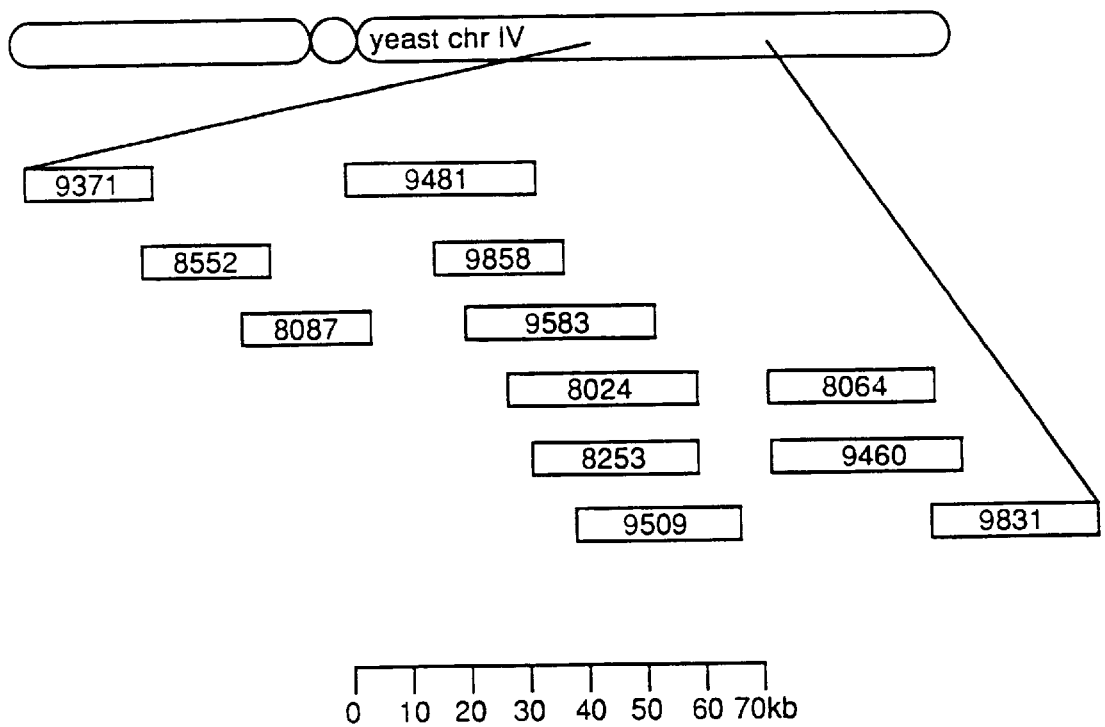
FIG. 6 shows a portion of known map of a yeast chromosomal library, illustrating the positions of each fragment of the library within yeast chromosome IV.

Accordingly, in a particularly preferred aspect of the present invention methods of genomic mapping are provided utilizing the sequence capturing methods already described. In particular, the methods of the present invention comprise identifying the Type-IIs and adjacent sequences (target sequences) on the individual fragments of a genomic library using the methods described above. FIG. 6 shows a genomic map for a portion of a yeast chromosome library, showing the overlap between the various fragments of the library.

The individual fragments of the library are treated using the above methods to capture the Type-IIs restriction sites and their adjacent ambiguous sequences. These captured sequences are then used as genetic markers, as described above, and a contig of the particular library may be assembled. In the preferred aspects, the captured Type-IIs and adjacent sequences will be hybridized to specific positionally oriented probes on the array. By determining the various probe sequences to hybridize with the captured sequences, these captured sequences are thereby determined.

The combination of these mapping techniques with oligonucleotide arrays provides the capability of identifying a large number of genetic markers on a particular sequence. Typically, a genomic fragment will have more than one, and even several Type-IIs restriction sites within its sequence.

Thus, when probed with an oligonucleotide array, the captured sequences from a particular genomic fragment will hybridize with a number of probes on the array, producing a distinctive hybridization pattern. Each hybridization pattern will generally comprise hybridization signals which correspond to each of the captured sequence markers in the fragment.

When repeated on separate fragments from the library, each fragment will generally produce a distinctive hybridization pattern, which reflects the sequences captured using the specific type-IIs capture method. These hybridization patterns may be compared with hybridization patterns from differentially generated fragments. Where a specific marker is present in both fragments, it is an indication of potential overlap between the fragments. Two fragments that share several of the same Type-IIs sequences, e.g., overlapping fragments, will show similar hybridization patterns on the oligonucleotide array.

The greater the similarity or correlation between two fragments, the higher the probability that these fragments share an overlapping sequence. By correlating the hybridization pattern of each fragment in the library against each other fragment in the library, a single contiguous map of the particular library can be constructed.

Figure 7A:
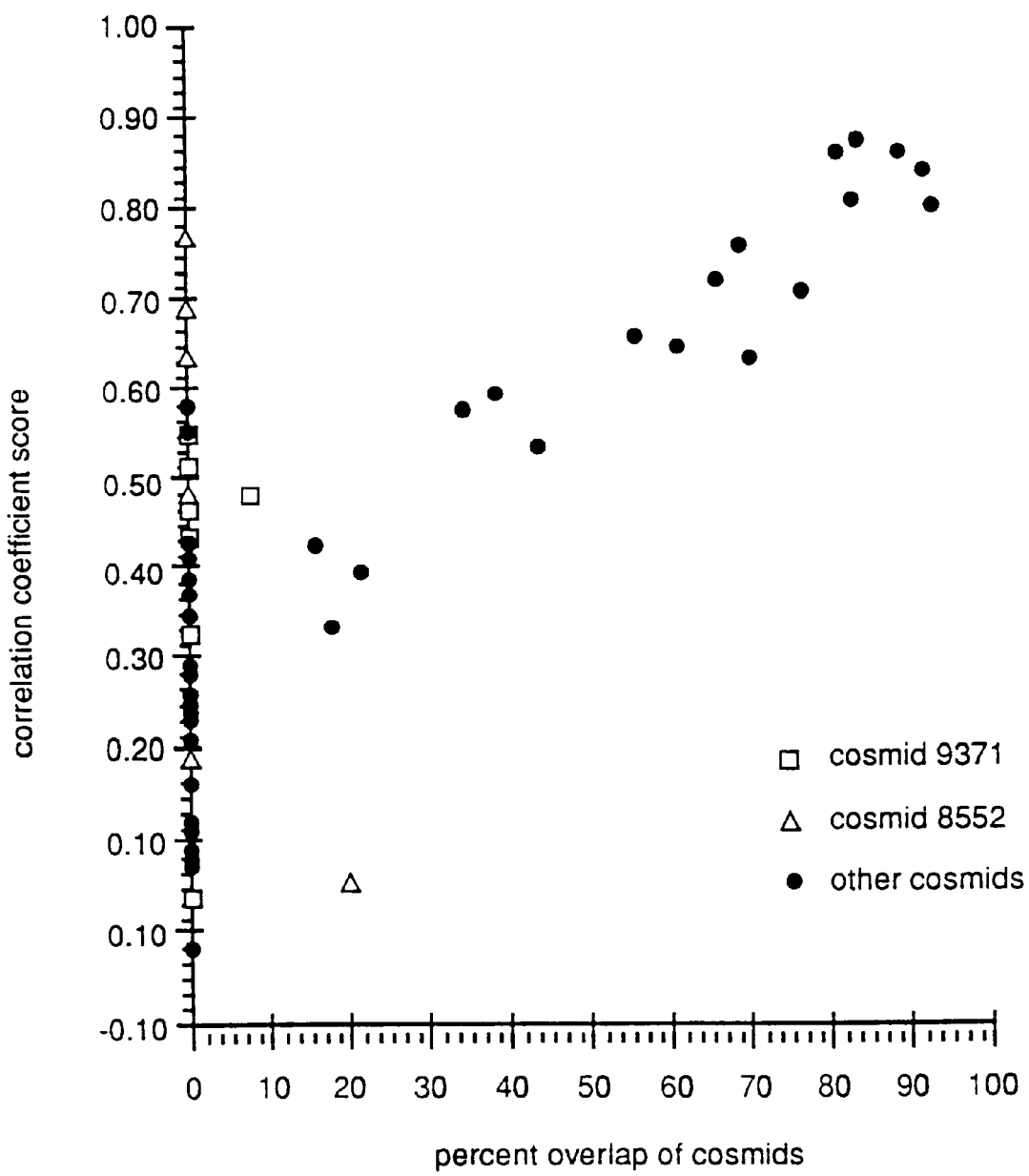
FIG. 7A shows a plot of correlation coefficient scores among hybridization patterns of yeast chromosomal fragments when using Type-IIs and adjacent sequences as markers.

In practice, each fragment is correlated to each other fragment, and a correlation score is given based upon the number of probes which cross-hybridize with the Type-IIs and adjacent sequences of both the first and second fragment. High scores indicates high overlap. For example, a perfect overlap, i.e., the comparison of two identical sequences would produce a correlation score of 1. Similarly, sequences sharing no overlapping sequence would, ideally, produce a correlation score of 0. However, in practice, sequences that do not overlap will generally have correlation scores above zero, due to potential non-specific hybridizations, e.g., single base mismatches, background hybridization, duplicated sequences, which may provide some baseline correlations between otherwise unrelated fragments. As a result, a cutoff may be established below which correlation scores are not used. The precise cutoff may vary depending upon the level of nonspecific hybridizations for the particular application. For example, by using capture methods that cut less frequently, and/or capture a greater number of sequences, the potential for duplicated markers is substantially reduced, and the cutoff may be lower. Correlation scores among all of the fragments may then be extrapolated to provide approximate percent overlap among the various fragments, and from this data, a contiguous map of the genomic library can be assembled (FIG. 7A). Additionally, one of skill in the art will appreciate that a more stringent determination of cosmid overlap may be obtained by repeating the capture and correlation methods using a different enzyme system, thereby generating additional, different markers and overlap data.

The combined use of sequence based markers and oligonucleotide arrays, as described herein, provides a method for rapidly identifying a large number of genetic markers and mapping very large nucleic acid sequences, including, e.g., cosmids, chromosome fragments, YACs and the like.

The present invention also provides methods for diagnosing a genetic disorder wherein said disorder is characterized by a mutation in a sequence adjacent to a known Type-IIs endonuclease restriction site using the methods described above. Specifically, sequences adjacent to Type-IIs restriction sites are captured and their sequence is determined according to the methods described above. The determined sequence is then compared to a "normal" sequence to identify mutations.

A. Genetic Linkage Mapping

Genetic linkage markers are defined as highly polymorphic sequences which are uniformly distributed throughout a genome. In an additional embodiment, the methods of the present invention are used to identify and define these polymorphic markers. Because these markers are identified and defined by their proximity to type-IIs restriction sites, they are referred to herein as restriction site sequence polymorphisms ("RSSPs"). In general, these RSSP markers are identified by comparing captured sequences among two genomes. The methods of the present invention may generally be used to identify these RSSPs in a number of ways. For example, a polymorphism within the recognition site of the type-IIs endonuclease will result in the presence of a captured sequence in one genome where it is absent in the other. This is generally the result where the polymorphism lies within the type-IIs recognition site, thereby eliminating the recognition site in the particular sequence, and, as a result, the ability to capture the adjacent sequences. It will be appreciated that the inverse is also true, that a polymorphism may account for the presence of a recognition site where one does not exist in the wild type. Second, a polymorphism may be identified which lies within the captured ambiguous sequence. These polymorphisms will typically be detected as a sequence difference between the compared genomes.

A wide variety of polymorphic markers may be identified for any given genome, based upon the type-IIs enzymes used for the first and second cleavages. For example, first cleavage enzymes which recognize distinct sequences will typically also define a number of distinct proximal polymorphisms.

The above described methods may be further modified, for example, using methods similar to those reported by Nelson, et al., Nature Genetics (1993) 4:11–18. Nelson, et al. report the identification of polymorphic markers using a system of genetic mismatch scanning. In the method of Nelson, et al., the genomes to be compared, e.g., grandchild and grandparent genomes, are first digested with an endonuclease which produces a 3' overhang, i.e., PstI. One of the two genomes is methylated at all GATC sites in the sequence (DAM+) while the other remains unmethylated (DAM−). The genomic fragments from each group are denatured, mixed with each other, and annealed, resulting in a mixture of homohybrids and heterohybrids. In the homohybrids, both strands will be either methylated or unmethylated, while in the heterohybrids, one strand will be methylated. The mixture is then treated with nucleases which will not cleave the hemimethylated nucleic acid duplexes, for example DpmI and MboI. Next, the mixture is treated with a series of mismatch repair enzymes, e.g., MutH, MutL and MutS, which introduce a single strand nick on the duplexes which possess single base mismatches. The mixture is then incubated with ExoIII, a 3' to 5' exonuclease which is specific for double stranded DNA, and which will degrade the previously digested homohybrids and the nicked strand of the mismatched heterohybrids, from the 3' side. Purification of the full dsDNA is then carried out using methods known in the art, e.g., benzoylated naphthoylated DEAE cellulose at high salt concentrations, which will bind ssDNA but not dsDNA. As a result, only the full-length, unaltered (perfectly matched) heterohybrids are purified. The recovered dsDNA fragments which indicate "identity by descent" (or "i.b.d.") are labelled and used to probe genomic DNA to identify sites of meiotic recombination.

Figure 8A:
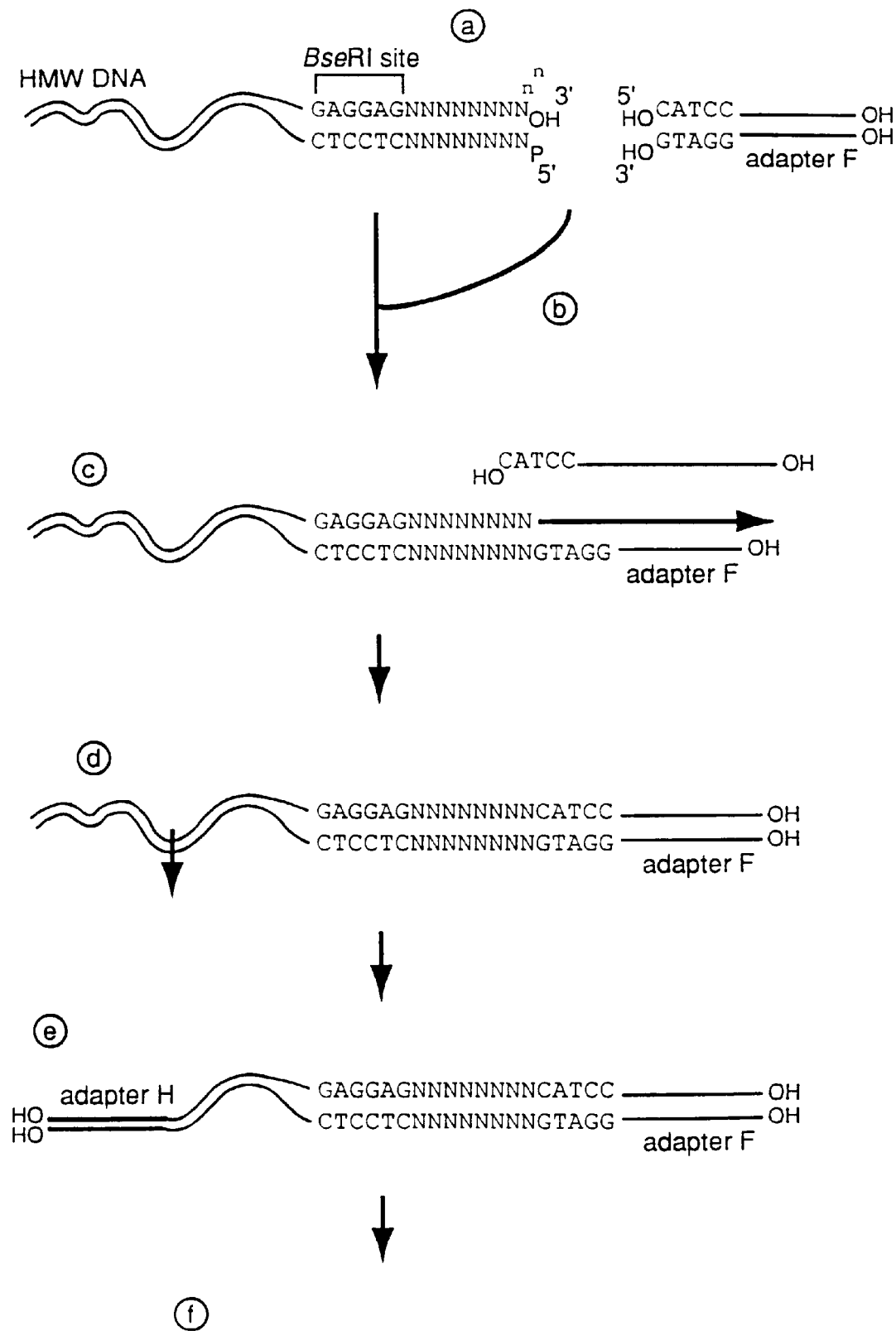
FIGS. 8A, 8B and 8C show a schematic representation of the identification of polymorphic markers, using the methods of the present invention.
Figure 8B:
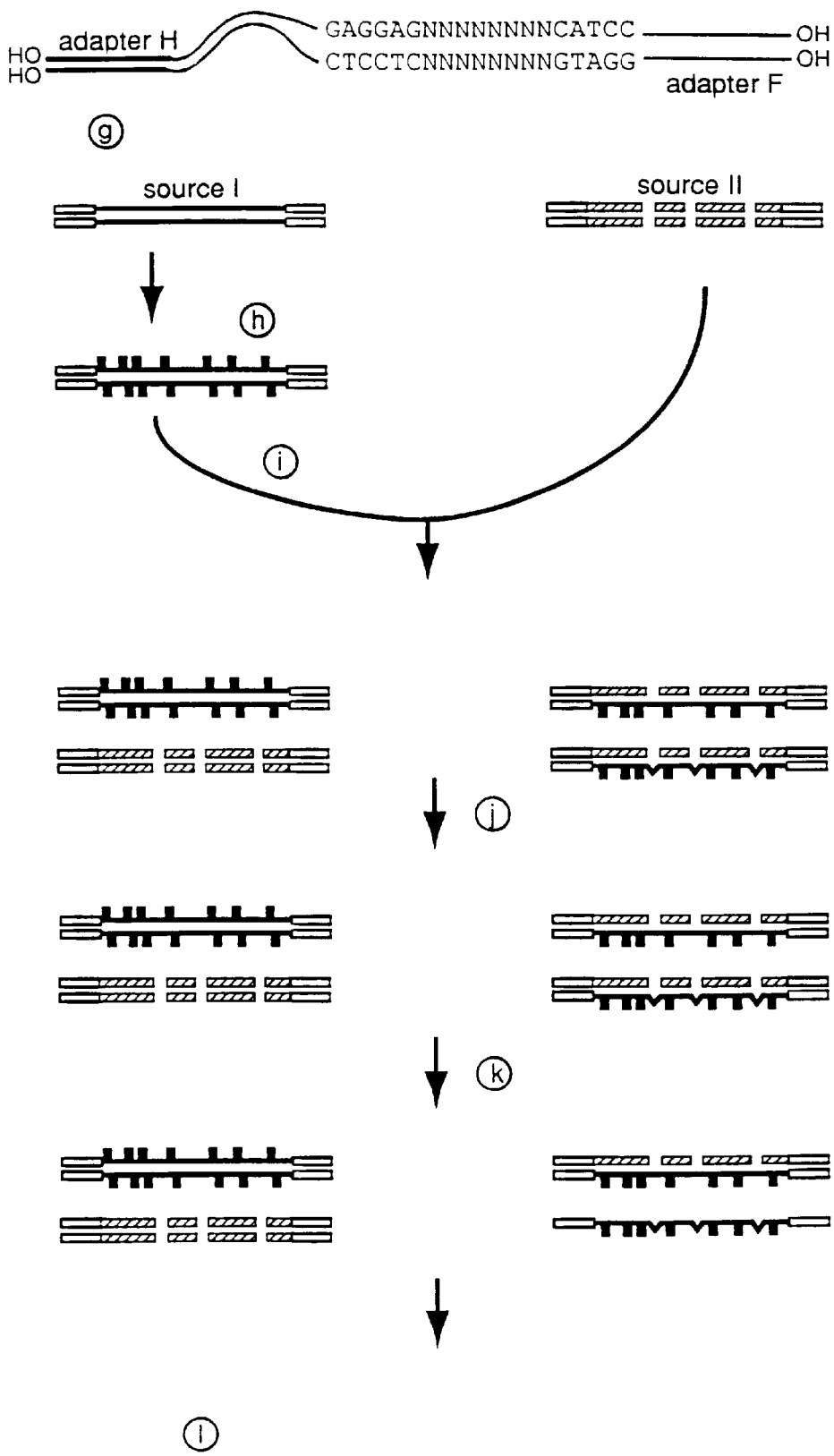
Figure 8C:
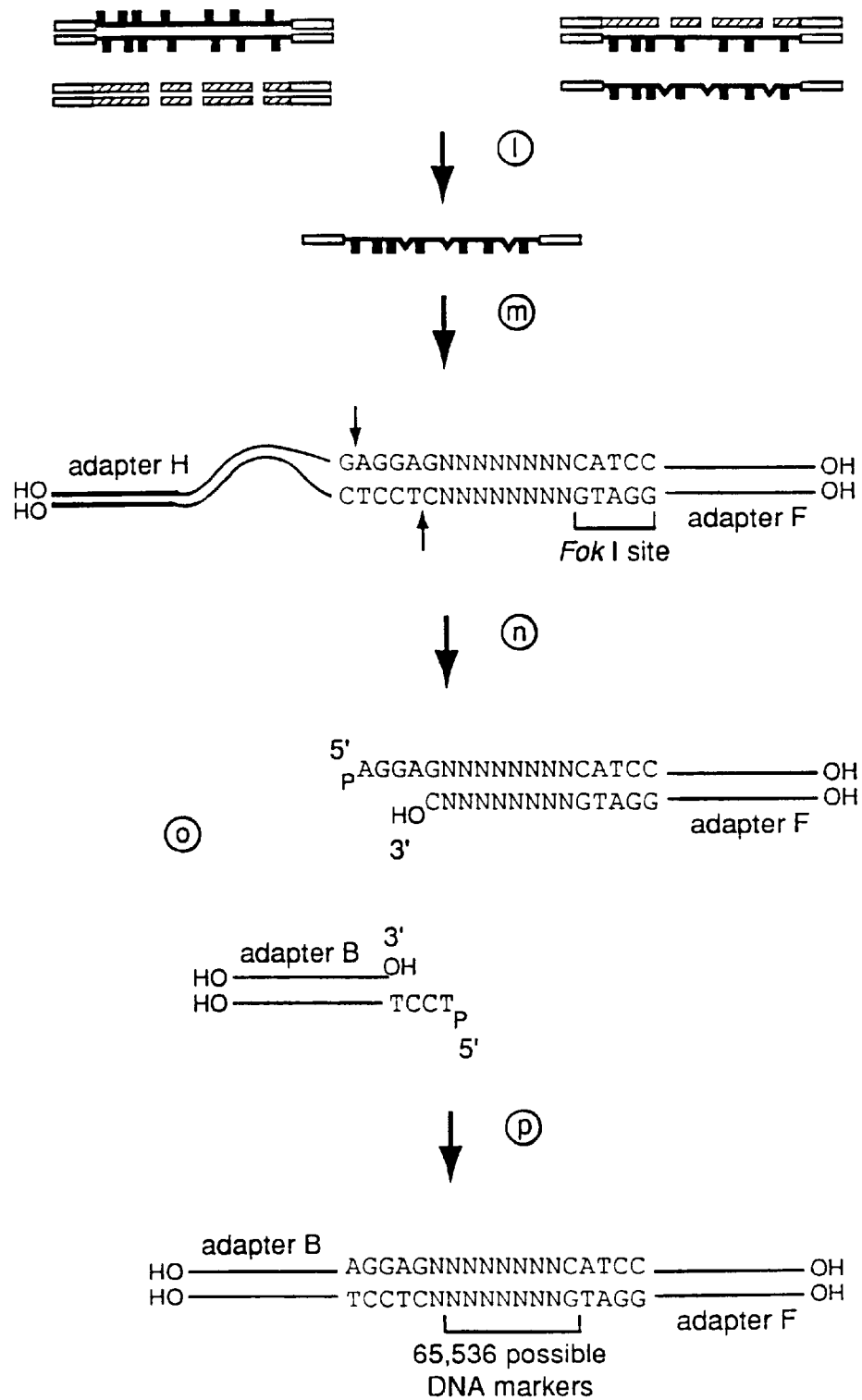

An adaptation of the above method can be applied to the capture methods of the present invention. In particular, the methods of the present invention can be used to capture sequences in the region of polymorphisms in a particular polynucleotide sequence. FIGS. 8A, 8B and 8C show a schematic representation of the steps used in practicing one embodiment of this aspect of the present invention. Specifically, a subset of genomic DNA which is identified by the presence of a type-IIs recognition site is amplified (FIG. 8A), DNA containing polymorphisms within the amplified subset are isolated (FIG. 8B), and the sequences adjacent to the type-IIs recognition site in the isolated polymorphism-containing sequences are identified and characterized (FIG. 8C).

Initially, polynucleotides from different sources which are to be compared, e.g., grandparent-grandchild, etc., are treated identically in parallel systems. These polynucleotides are each cleaved with a first type-IIs endonuclease, as is described in substantial detail above. In FIG. 8A, step (a), for example, this first cleavage is shown using BseR1. The specific Type-IIs enzyme used in this first cleavage may again vary depending upon the desired frequency of cleavage, the length of the target sequence, etc.

As previously described, a first adapter bearing a second type-IIs endonuclease recognition site is ligated to the cleaved polynucleotides (FIG. 8A, step (b)). In the example of FIG. 8A, steps (a), (b) and (c), this recognition site is that of the type-IIs endonuclease FokI. The polynucleotides are then cleaved with an endonuclease which will cleave upstream from the captured sequence and ligated first adapter, such as a type II endonuclease, e.g., HaeIII (see FIG. 8A, step (d)). Typically, this second cleavage enzyme will be selected whereby it cleaves more frequently than the first Type-IIs enzyme. A second adapter sequence may then be ligated to this new cleavage site (FIG. 8A, step (e)). The entire sequence, including the two adapter sequences is then typically amplified (FIG. 8A, step (f)). The amplification is facilitated in preferred aspects by incorporating a primer sequence within the adapter sequences.

The amplified polynucleotides from each source is isolated (FIG. 8B, step (g)). The polynucleotide from one source is then methylated (FIG. 8B, step (h)). Both the methylated polynucleotide from the first source and the unmethylated polynucleotide from the second source are mixed together, heated to denature duplex DNA, and reannealed (FIG. 8B, step (i)). This generally results in a mixture of hemimethylated heterohybrids having one strand from each source, homohybrids of unmethylated dsDNA and homohybrids of fully methylated dsDNA. At this point, unlike the method of Nelson, et al. (DpmI and MboI additions are omitted), the mixture is treated with the mismatch repair enzymes, e.g., MutLSH, which will nick only hemimethylated, mismatched hybrids, leaving the homohybrids and perfectly matched heterohybrids untouched (FIG. 8B, step (j)). The nicked DNA is then digested, as in Nelson, et al., with an exonuclease, e.g., ExoIII (FIG. 8B, step (k)). The mixture will then contain dsDNA which is fully methylated, i.e., homohybrids of DNA from one source, dsDNA which is unmethylated, i.e., homohybrids of DNA from the other source, heterohybrids of dsDNA from both sources, but which are perfectly matched, i.e., contains no mismatches or polymorphisms, and ssDNA, i.e., the DNA which is left from the heterohybrid, mismatched or polymorphic dsDNA. This ssDNA reflects the polymorphism and may then be purified from the dsDNA using the methods described in Nelson, et al., e.g., purification over benzoylated naphthoylated DEAE cellulose in high salt (FIG. 8C, step (1)).

The purified single stranded DNA is then reamplified to dsDNA using methods well know in the art, e.g., PCR (FIG. 8C, step (m)). The amplified DNA may then cleaved with a second type-IIs endonuclease which recognizes the site incorporated into the first adapter sequence, as described above (FIG. 8C, step (n)), followed by ligation of another adapter sequence to the cleavage end (FIG. 8C, step (o)). The captured sequence thus identifies a polymorphism is which lies between the captured sequence and the upstream cleavage site. The captured sequence may then be determined according to the methods described herein, e.g., amplification, labelling and probing (FIG. 8C, step (p)).

IV. Applications

The methods described herein are useful in a variety of applications. For example, as is described above, these methods can be used to generate ordered physical maps of genomic libraries, as well as genetic linkage maps which can be used in the study of genomes of varying sources. The mapping of these genomes allows further study and manipulation of the genome in diagnostic and therapeutic applications, e.g., gene therapy, diagnosis of genetic predispositions for particular disorders and the like.

In addition to pure mapping applications, the methods of the present invention may also be used in other applications. In a preferred embodiment, the methods described herein are used in the identification of the source of a particular sample. This application would include forensic analysis to determine the origin of a particular tissue sample, such as analyzing blood or other evidence in criminal investigations, paternity investigations, etc. Additionally, these methods can also be used in other identification applications, for example, taxonomic study of plants, animals, bacteria, fungi, viruses, etc. This taxonomic study includes determination of the particular identity of the species from which a sample is derived, or the interrelatedness of samples from two separate species.

The various identification applications typically involve the capturing and identification of sequences adjacent specific type-IIs restriction sites in a sample to be analyzed, according to the methods already described. These sequences are then compared to sequences identically captured and identified from a known source. Where sequences captured from both the sample and the source are identical or highly similar, it is indicative that the sample was derived from the source. Where the sequences captured from the sample and known source share a large number of identical sequences, it is indicative that the sample is related to the known source. However, where the sample and source share few like sequences, it is indicative of a low probability of interrelation.

Precise levels of interrelation to establish a connection between source and sample, i.e., captured sequence homology, will typically be established based upon the interrelation which is being proved or disproved, the identity of the known source, the precise method used, and the like. Establishing the level of interrelation is well within the ordinary skill in the art. For example, in criminal investigations, a higher level of homology between sample and known source sequences will likely be required to establish the identity of the sample in question. Typically, in the -criminal context, interrelation will be shown where there is greater than 95% captured sequence homology, preferably greater than 99% captured sequence homology, and more preferably, greater than 99.9% captured sequence homology. For other identification applications, interrelation between sample and known source may be established by a showing of, e.g., greater than 50% captured sequence homology, and typically greater than 75% captured sequence homology, preferably greater than 90% captured sequence homology, and more preferably greater than 95 to 99% captured sequence homology.

The level of interrelation will also typically vary depending upon the portion of a genome or nucleic acid sequence which is used for comparison. For example, in attempting to identify a sample as being derived from one member of a species as opposed to another member of the same species, it will generally be desirable to capture sequences in a region of the species' genetic material which displays a lower level of homology among the various members of the same species. This results in a higher probability of the captured sequences being specific to one member of the species. The opposite can be true for taxonomic studies, i.e., to identify the genus and species of the sample. For example, it may generally be desirable to select a portion of the genetic material of the known genus or species which is highly conserved among members of the genus and/or species, thereby permitting identification of the particular sample to that genus or species.

The present invention is further illustrated by the following examples. These examples are merely to illustrate aspects of the present invention and are not intended as limitations of this invention. The methods used generally employ commercially available reagents or reagents otherwise known in the art.

EXAMPLES

Example 1

1. Digesting High Molecular Weight DNA with EarI

4 μg of λ DNA was treated with 4 units of EarI in 10 μl at 37° C., for 4 hours. The reaction was then heated to 70° C. for 10 minutes. Cleavage was verified by running 5 μl of the sample on an agarose gel to determine complete cleavage. The remaining 5 μl was brought to 40 μl (final concentration of 50 ng/μl λ DNA).

2. Klenow Fill-in Reaction

4 μl of the digested λ DNA was added to 0.5 μl of 10× Klenow Buffer, 0.5 μl 2 mM dNTPs, and 0.05 μl of 0.25 units of Klenow fragment. The reaction mixture was incubated for 20 minutes at 25° C., followed by 10 minutes at 75° C. Similar results were also obtained using T4 DNA polymerase for the fill-in reaction.

3. Preparing Adapter Sequences

Two separate adapter sequences were prepared, adapter sequence 1 and adapter sequence 2. Adapter sequence 1 is used in the first ligation reaction whereas adapter 2 is used for the second. As each adapter and its ligation are somewhat different, they are addressed separately.

Double stranded adapter 1 comprising the second Type-IIs endonuclease restriction site 3' C-G-C-A-G- . . . 5' and a T7 promoter sequence was prepared by adding 10 μl each of 10 μM unphosphorylated T7 strand and its complement, heating the mixture to 95° C., then cooling over 20 minutes to anneal the strands. The strands were prepared using DNA synthesis methods generally well known in the art. The resulting mixture had a final dsDNA adapter concentration of 5 μM.

Adapter 2 comprising the overhang complementary to that created by the HgaI digestion of the target sequence, as well as a T3 promoter sequence was prepared by first creating the overhang region. A single stranded oligonucleotide of the sequence 3'. . .-G-A-G-A-A 5' was synthesized on a single stranded T3 promoter sequence. The final concentration of reagents is shown in parentheses. The 5' end of this sequence was then phosphorylated as follows: 10 μl of 10 μM the oligonucleotide (5 μM), 2 μl of 10× kinase buffer (1×), 2 μl 10 mM ATP (1 mM), 5 μl water and 1 μl T4 polynucleotide kinase (10 units) were added. The reaction was incubated at 37° C. for 60 minutes, then at 68° C., for 10 minutes and cooled.

To the T3/overhang ssDNA strand was added 10 μl of 10 μM appropriate antistrand and 3.33 μl of buffer. This mixture was heated to 95° C. and cooled over 20 minutes to anneal the two strands.

4. Ligation of First Adapter to Target Sequence

At least a 50:1 molar ratio of first adapter to cleavage ends was desired and an approximate ratio of 100:1 adapters to cleavage ends was targeted. As λ DNA digested with EarI is known to result in 34 pairs of cleavage ends, a 3400:1 mole ratio of adapters to λ DNA was used.

In 11 μl total reaction mixture, the following were combined, 5 μl from the fill-in reaction (approx. 40 nmoles target DNA), 4 μl of 5 μM first adapter (2 μM final concentration), 1.1 μl 10× ligation buffer (1× final concentration), and 1 μl of T4 DNA ligase (400 units final concentration).

The reaction was incubated at 25° C. for 2 hours, then incubated at 75° C. for 10 minutes to inactivate the ligase as well as dissociate unligated adapter strand.

5. Second Klenow Fill-in Reaction

Filling in the single stranded portion of the target sequence/first adapter created by dissociation of the unligated strand in step 4 above, was accomplished using the Klenow fragment DNA polymerase.

In 14 μl total was added 11 μl of DNA to which the first adapter had been ligated (approx. 34.4 μM total adapted ends), 1.5 μl 10× Klenow buffer (1×), 1.5 μl 2 mM dNTPs (50 μM each dNTP) and 0.05 μl Klenow fragment (0.25 units). This mixture was incubated at 37° C. for 30 minutes, then heated to 75° C. for 10 minutes. Again, similar results were obtained using *E. coli* DNA polymerase.

6. Second Digestion with HqaI

To the 14 μl reaction mixture of step 6 was added 1 μl of HgaI (2 units). The reaction was incubated at 25° C. for 3 hours. 1.6 μl of 5 M NaCl (0.5 M) was then added to raise the melting point of the target sequence to above 70° C. The reaction mixture was then heated to 65° C. for 20 minutes.

7. Ligation of Second Adapter to Target Sequence

The 16 μl reaction mixture from step 7 is expected to have an approximate concentration of 4.4 nM target sequence with compatible ends for the second ligation. This number is halved from the expected concentration of total target sequence. This was to account for the blunt end ligation of adapter 1 in the reverse orientation such that HgaI cleavage would not occur.

To the 16 μl reaction mixture from step 7, was added 5 μl of 3 μM second adapter prepared in step 3, above (0.3 μM), 5 μl 10× ligation buffer (10×), 23.5 μl water and 0.5 μl T4 DNA ligase (200 units). The reaction mixture was incubated at 37° C. for 30 minutes then heated to 65° C. for 10 minutes.

8. PCR Amplification

5μl of the captured target sequence from step 7 is used as the template for PCR amplification (approx. 440 pM total; 14.7 pM each end). To this was added 1.25 μl each of 10μM T7 primer, and 10 μM T3 primer (0.25 μM primer), 5 μl 10× PCR buffer (10×), 5 μl 4×2 mM dNTPs (200 μM each dNTP), 24.5 μl water and 0.5 μl Taq polymerase (2.5 units).

PCR was carried out for 40 cycles of 94° C. for 30 seconds, 55° C. for 30 seconds and 72° C. for 30 seconds. Controls were run using water, λ DNA cut with EarI and uncut λ DNA subjected to steps 1–7. 2 μl from the reaction was run on a 4% NuSieve® Agarose gel, indicating a 62-bp amplicon which is carried into the next step.

9. Labelling-Asymmetric PCR

The 62-bp amplicon produced in step 8 is next labeled with a 5'-F label by asymmetric PCR.

44 µl of the PCR amplicon from step 8 (50 fmoles) is mixed with 5 µl of 10 µM T7-5' F primer (1 µM primer), 2 µl of 10× PCR buffer (1× buffer), 3 µl of 100 mM MgCl$_2$ (5 mM), 5 µl of 4×2 mM dNTPs (200 mM each dNTP) and 0.5 µl Taq polymerase (2.5 units).

PCR was carried out for 40 cycles as described in step 8. 3 µl from this reaction was the run on 4% NuSieve® Agarose gel and compared to the amplicon from step 8 to confirm florescent labelling.

9. Results

Figure 4:
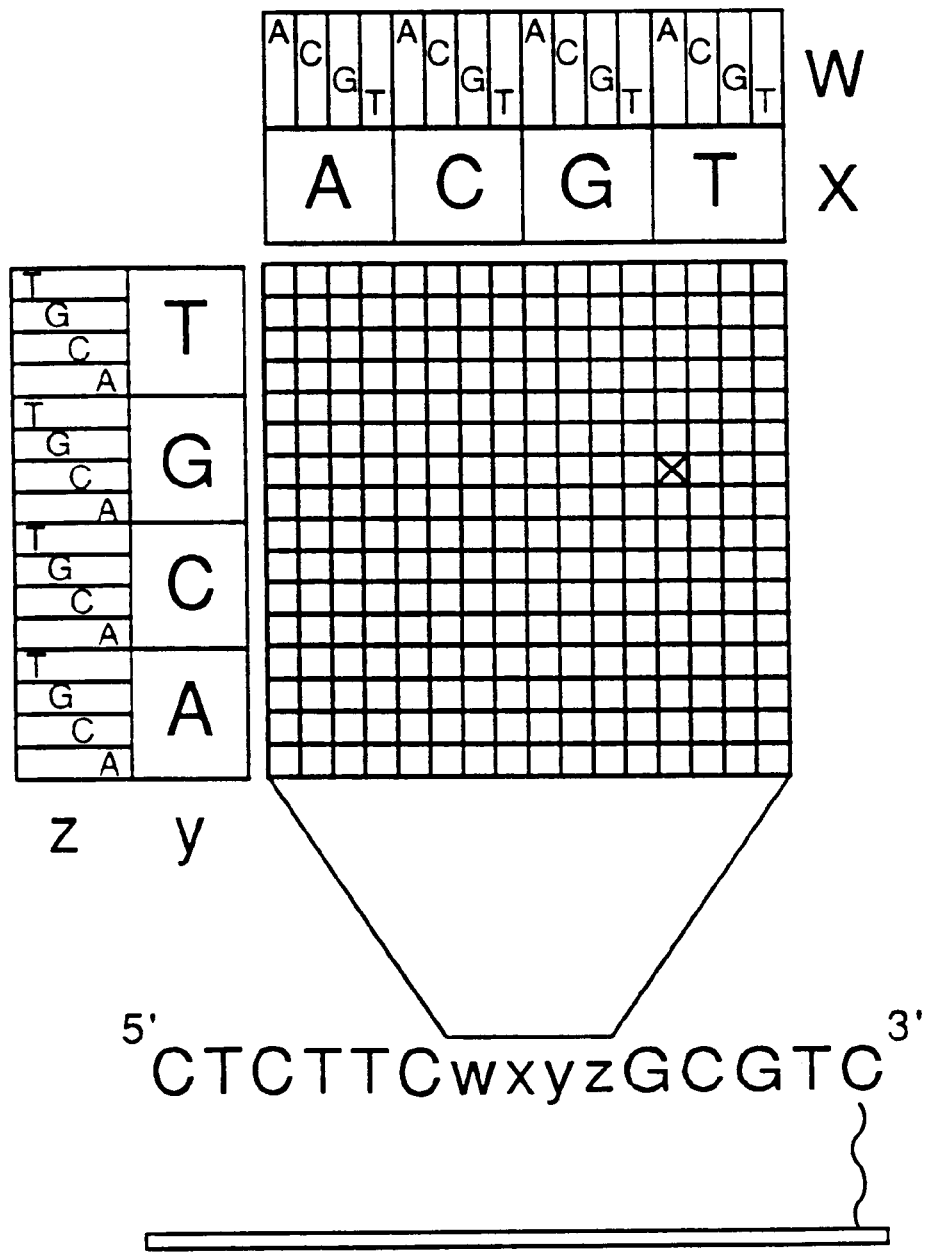
FIG. 4 shows the combinatorial design for an oligonucleotide array used to probe a four nucleotide captured ambiguous sequence. The probes upon the array are 15mers having the sequence 3' C-T-G-C-G-w-x-y-z-C-T-T-C-T-C 5', where - w-x-y-z- are determined by the probe's position on the array. For example, the probe indicated by the darkened square on the array shown will have the w-x-y-z sequence of - A-T-G-C-.
Figure 5:
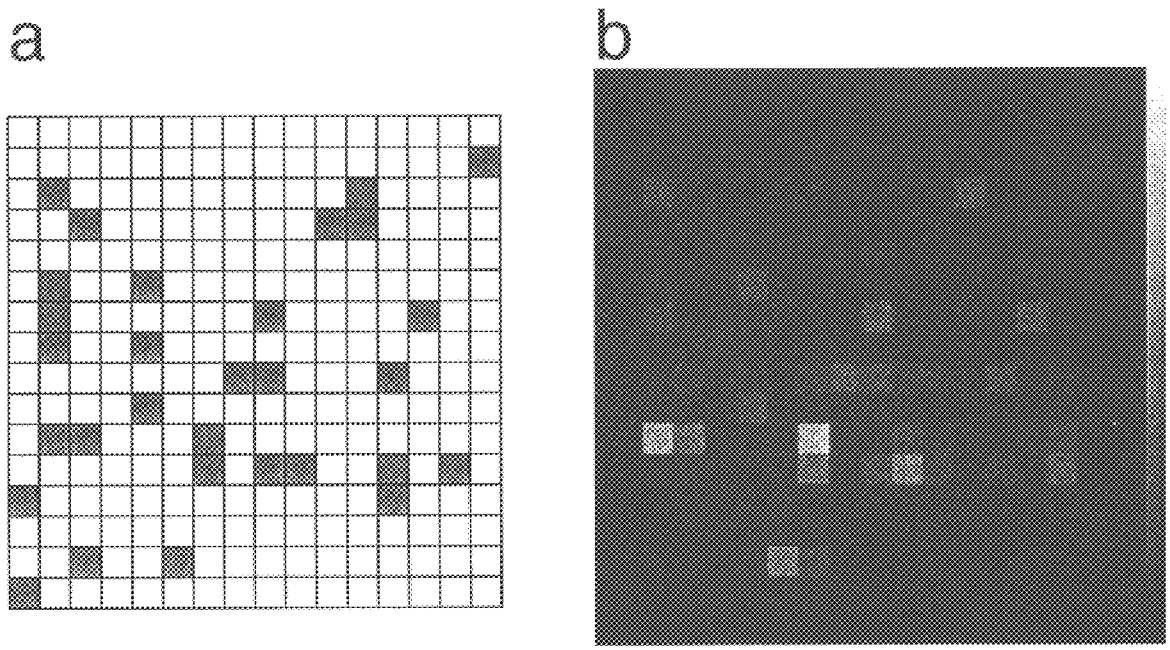
FIG. 5A and 5B show the predicted and actual fluorescent hybridization pattern of captured sequences from λ DNA as described in Example 1 upon an oligonucleotide array probe having the combinatorial design of FIG. 4. Panel A shows the predicted hybridization pattern where the darkened squares indicate expected marker/probe hybridizations from captured sequences from λ DNA cut with EarI and captured with HgaI bearing adapter sequences. The actual fluorescence of the hybridization is shown in panel B.

The florescent captured sequence was heated to 95° C. briefly, then buffered with 6× SSPE, 10 mM CTAB and 0.2% Triton X-100. The captured sequence was then probed on an oligonucleotide array having the combinatorial array shown in FIG. 4. FIG. 5, panel A shows the expected hybridization pattern of λ DNA to the array of FIG. 4 as denoted by the blackened regions on the array. FIG. 5, panel B illustrates the actual hybridization pattern of captured Type-IIs sites from λ DNA on an array as shown in FIG. 4. The close correlation between expected and actual hybridization is evident.

Example 2

The above capture methods were applied to a genomic library of 12 known cosmids from yeast chromosome IV. The clones have been previously physically mapped using EcoRI-HindIII fragmentation. The specific library, including known map positions and overlap of the 12 cosmids, is illustrated in FIG. 6.

The twelve genomic clones were constructed in a pHC79 vector, in E. coli host HB101. Cosmid DNA was prepared from 3 ml cultures by an alkaline lysis miniprep method. The miniprep DNA was digested with EcoRI and HindIII to confirm the known fingerprint of the large cloned inserts. Cosmid DNA was treated with linear DNAase, Plasmid-Safe™ DNAse, at 37° C. for 15 minutes, followed by heat inactivation. The DNAse treatment was carried out to remove any potential spurious EarI digested sites resulting from contaminating bacterial DNA. This leaves cosmid DNA substantially untouched. After confirming the presence of clean banding cosmid DNA, the resulting cosmids were then subjected to the capture methods described above. The pCH79 vector, without a yeast insert, was transformed into HB101 and isolated as a miniprep, to serve as a control.

The data from the array was normalized as follows. First, the probe array was normalized for background intensity by subtracting the background scan (hybridization buffer with no target). Second, the data was normalized to the specific vector used in producing the cosmids. Normalization to the vector had two parts: first the average intensity of four hybridizing markers present in pHC79 vector was calculated for each scan, for use as an internal control in that scan. This intensity was divided into all intensities in that scan, and second the overall background intensity of the pCH79 vector in a bacterial host, absent a yeast insert, was subtracted. The array signal was normalized for relative hybridization of the probes on the array, by using equimolar target mixtures for each probe. Finally, the four values corresponding to the pCH79 markers were discarded.

The resulting hybridization patterns were then correlated, pair-wise, between all cosmids. Specifically, the signal intensity for each probe was compared among the same probe's intensity for all other fragments. Where the signals were the same, there was some correlation. The more signals that were the same, the higher the correlation score.

These correlation scores are plotted against the known percent overlap for these cosmids as determined from the EcoRI/HindIII physical map. This plot is shown in FIG. 7A. As is apparent, the correlation of hybridization scores between fragments is readily correlatable to percent overlap of the fragments.

Example 3-Simulated Annealing

The correlation scores from yeast chromosome IV, above, were used to construct a best fitting contig, using the simulated annealing process as described by Cuticchia, et al., The use of simulated annealing in chromosome reconstruction experiment based on binary scoring, Genetics (1992) 132:591–601. A global maximum was sought for the sum of correlation coefficient scores for a given sequence of cosmids in the randomly constructed and permutated contig. The resulting high scoring contigs for all 12 cosmids and for the 10 "strong-signal" cosmids are shown below. Each cosmid was assigned a rank based upon the known position of that cosmid, and these are as follows:

TABLE 1

| Cosmid Number | Cosmid Rank |
| --- | --- |
| 9371 | A |
| 8552 | B |
| 8087 | 1 |
| 9481 | 2 |
| 9858 | 3 |
| 9583 | 4 |
| 8024 | 5 |
| 8253 | 6 |
| 9509 | 7 |
| 9460 | 8 |
| 8064 | 9 |
| 9831 | 10 |

Simulated annealing of all twelve cosmids produced the following ordering:

(1 2 3 4) (7 6 5) A B (8 9 10)

Inclusion of the weaker signal cosmids, A and B, results in some shuffling of the predicted order of the cosmids. Removal of cosmids A and B, the "weak-signal"cosmids, produced the following ordered map of the remaining ten cosmids:

(1 2 3 4 5 6 7) (8 9 10)

which reflects the proper ordering and indicates the existence of the two "islands" of cosmids as seen in the physical map.

Figure 7B:
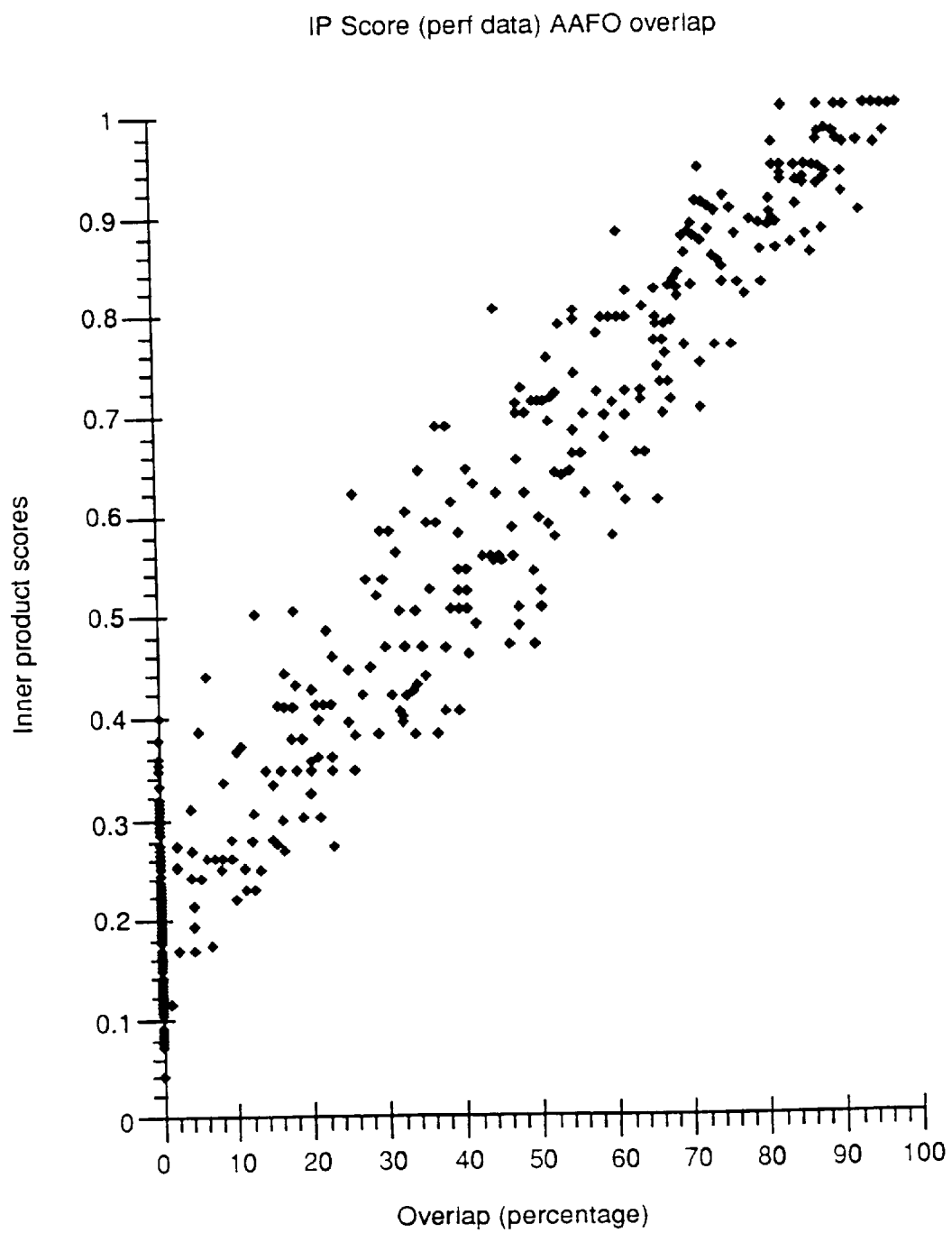
FIG. 7B shows the predicted "correlation" scores for EarI captured marker sequences for fifty simulated sequences from yeast chromosome III. The inner product scores for pair-wise comparison of the sequences is plotted versus the percent overlap of the sequences.

As can be seen, the inclusion of the weaker signal cosmids A and B, 8552 and 9731, inverts the order of clones in the center positions (5, 6 and 7), and improperly places Example 4-Simulated Mapping of Yeast Chromosome III To determine how well the distribution of points in FIG. 7A matches the distribution of scores expected for a random set of yeast cosmids, a random set of fifty 35 to 40 kb sequences from yeast chromosome III ("YCIII") were simulated. A list of perfect matches corresponding to EarI associated tetramers was also generated. Due to the difficulty in assigning simulated intensity scores for these markers, the marker probes were scored as 1, and 0 for non marker probes. Inner product scores were used instead of correlation coefficients to determine the similarity of the marker sets in 1225 comparisons of the fifty simulated YCIII cosmids. The scores were plotted against expected overlap, and this is shown in FIG. 7B. Even when perfect information regarding marker identities in the tetramer sets is compared, a certain amount of scatter is seen in the plot. Additionally, comparison of sequences with no overlap generate inner product scores ranging from 0.05 to 0.4. These two features are characteristic of the actual data shown in FIG. 7A.

Figure 7C:
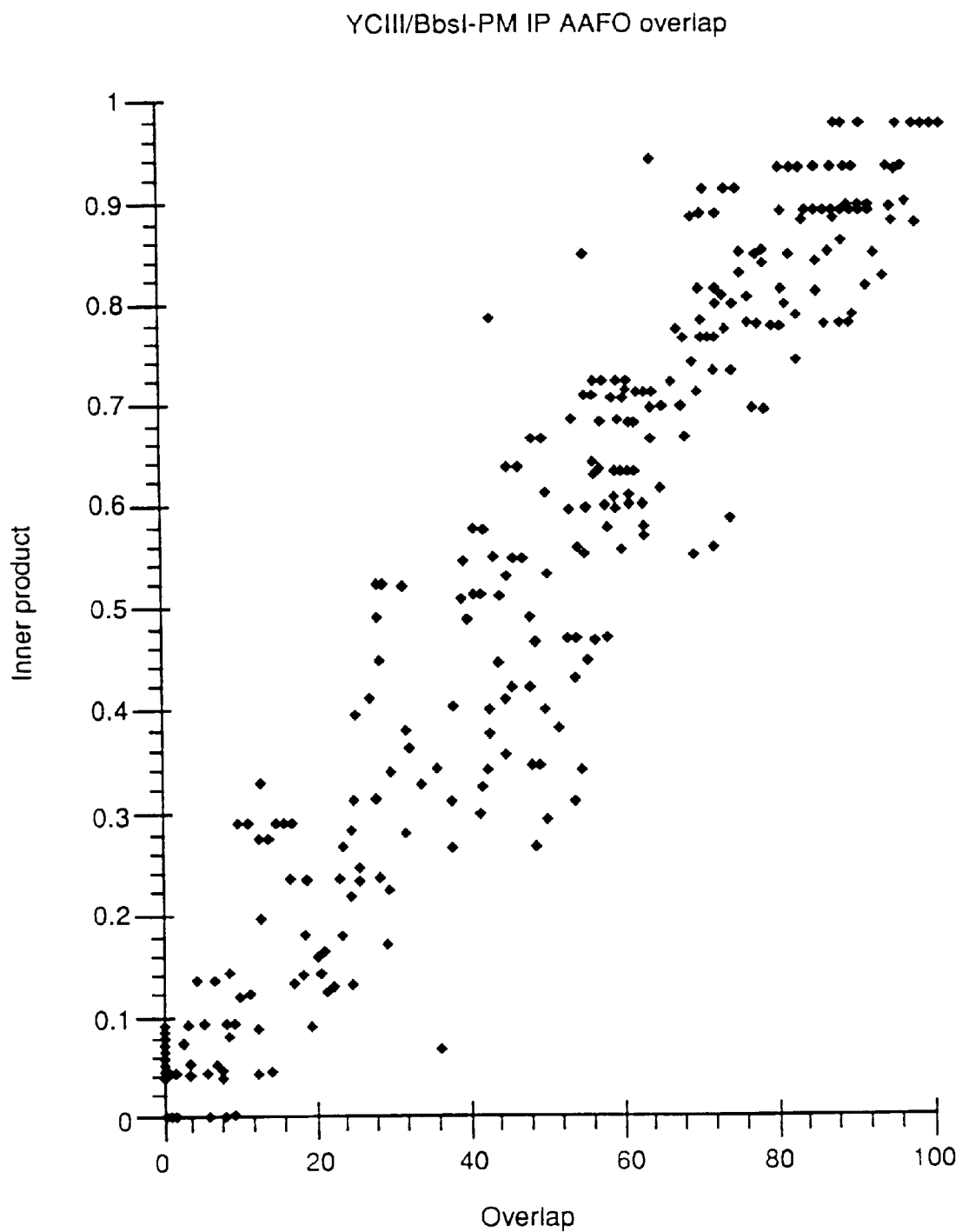
FIG. 7C shows the same simulated correlation using BbsI captured marker sequences.
Figure 7D:
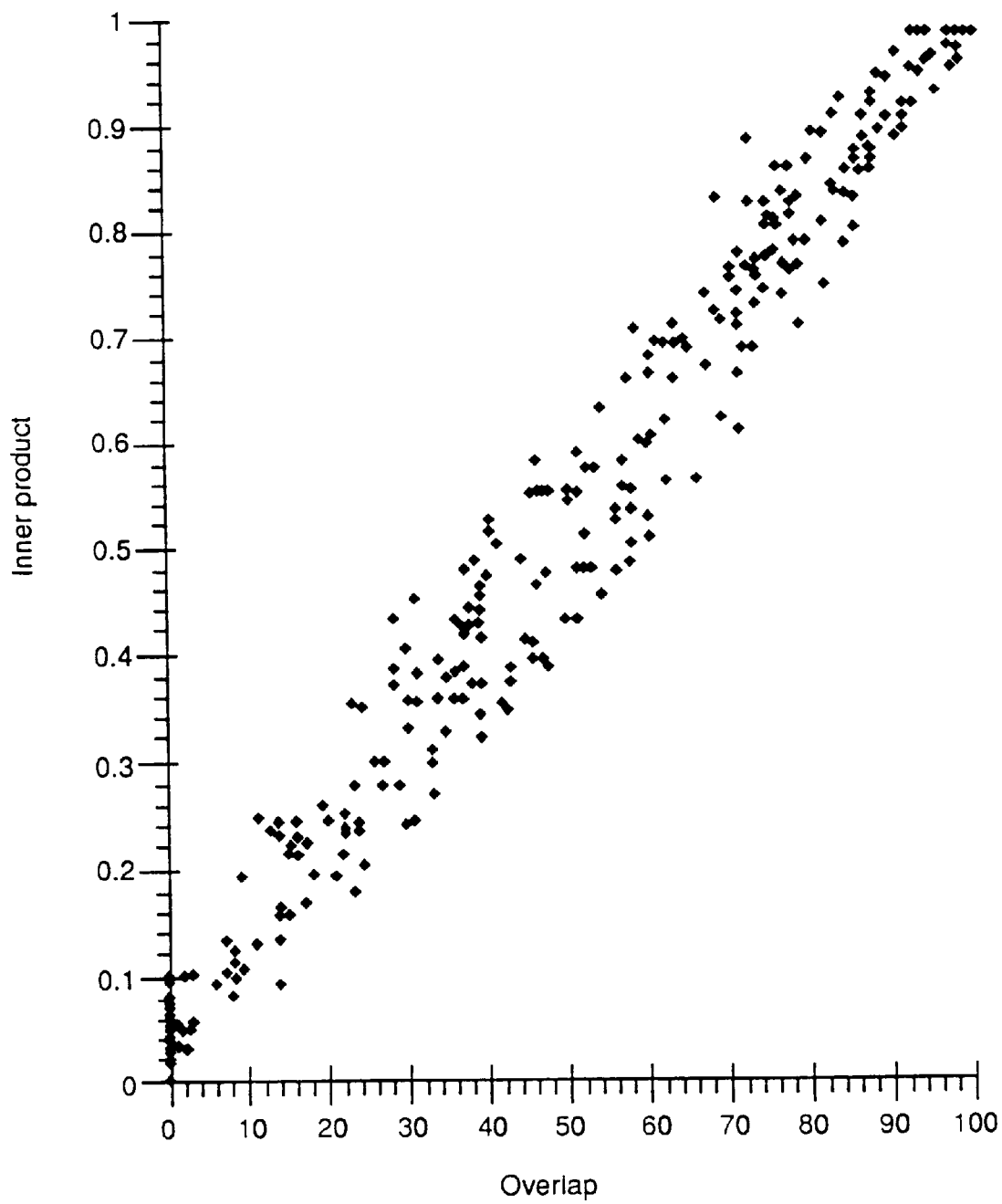
FIG. 7D shows a simulated correlation using HphI captured marker sequences.

The simulation was repeated using BbsI and HphI as the first cleaving enzyme, and the results are shown in FIGS. 7C and 7D, respectively. From this data, it can be seen that the amount of scatter in a particular plot is a function of the inverse of the frequency of cleavage sites (e.g., number of markers) in the target sequence. In particular, using HphI as the first cleaving enzyme would produce 564 markers in YCIII, whereas BbsI would yield 212 and EarI would yield 274. The scatter for the more frequently cutting HphI enzyme is substantially less than that for BbsI and EarI. Additionally, as noted previously, the Y intercept is also affected by the number of markers in the target sequence, as well as the frequency of a particular marker (e.g., marker duplication). Both of these factors may be influenced by the choice of capture methods and enzymes.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents. All publications and patent documents cited in this application are incorporated by reference in their entirety for all purposes to the same extent as if each individual publication or patent document were so individually denoted.

What is claimed is:

1. A nucleic acid adapter comprising a type IIs endonuclease recognition sequence positioned in the adapter such that on joining the adapter to a second nucleic acid, and treating with the type IIs endonuclease, the type IIs endonuclease cuts within both strands of the second nucleic acid without cutting the adapter.

2. The adaptor of claim 1, wherein the type IIs endonuclease is selected from the group consisting of HgaI, BbvI, BspMI, BsmFI and FokI.

3. The adapter of claim 1, further comprising a primer or promoter sequence.

4. A method of isolating a fragment of a target nucleic acid, comprising:
   ligating the target nucleic acid to a nucleic adapter comprising a type IIs endonuclease recognition sequence to form a recombinant nucleic acid, wherein the type IIs recognition sequence is positioned in the adapter such that on joining the adapter to the target nucleic acid, and treating with the type IIs endonuclease, the type IIs endonuclease cuts the target nucleic acid without cutting the adapter; and
   cleaving the recombinant nucleic acid with the type IIs restriction endonuclease to form a further recombinant nucleic acid comprising the adapter linked to a fragment of the target.

5. The method of claim 4, wherein the type IIs endonuclease is selected from the group consisting of HgaI, BbvI, BspMI, BsmFI and FokI.

6. The method of claim 4, wherein the adapter further comprises a primer or promoter, and wherein the method further comprises amplifying the further nucleic acid.

7. The method of claim 4, further comprising hybridizing the further recombinant nucleic acid to an array of probes.

8. The method of claim 4, wherein each of a population of target nucleic acids are joined to the adapter, and the cleaving step forms a population of further nucleic acids.

9. The method of claim 8, further comprising hybridizing the population of further nucleic acids to an array of probes to generate a hybridization pattern.

10. The method of claim 9, further comprising repeating the joining, cleaving and hybridizing steps with a second population of differentially generated target sequences to generate a second hybridization pattern, and comparing the hybridization pattern and the second hybridization pattern.

* * * * *